(12) United States Patent
Peter et al.

(10) Patent No.: US 8,174,698 B2
(45) Date of Patent: May 8, 2012

(54) MEMS TUNABLE SILICON FABRY-PEROT CAVITY AND APPLICATIONS THEREOF

(75) Inventors: Yves-Alain Peter, Terrebonne (CA); Jonathan Masson, Lausanne (CH); Raphaël St-Gelais, Montreal (CA)

(73) Assignee: Corporation de l'Ecole Polytechnique de Montréal, Montreal (CA)

( * ) Notice: Subject to any disclaimer, the term of this patent is extended or adjusted under 35 U.S.C. 154(b) by 465 days.

(21) Appl. No.: 12/228,175

(22) Filed: Aug. 11, 2008

(65) Prior Publication Data

US 2009/0153844 A1 Jun. 18, 2009

Related U.S. Application Data

(60) Provisional application No. 60/935,417, filed on Aug. 10, 2007.

(51) Int. Cl.
*G01N 21/00* (2006.01)
(52) U.S. Cl. ........................... 356/432; 356/436
(58) Field of Classification Search .......... 356/432–448, 356/128–132; 372/9, 20; 359/333, 346, 359/337.5, 237, 238, 290; 430/269, 322, 430/323; 216/24
See application file for complete search history.

(56) References Cited

U.S. PATENT DOCUMENTS

| | | | | |
|---|---|---|---|---|
| 6,078,395 A * | 6/2000 | Jourdain et al. | ............... | 356/519 |
| 7,545,513 B2 * | 6/2009 | Kiesel et al. | ................... | 356/519 |
| 2005/0068627 A1* | 3/2005 | Nakamura et al. | ............ | 359/578 |
| 2010/0220331 A1* | 9/2010 | Zribi et al. | .................... | 356/454 |

OTHER PUBLICATIONS

Yun et al., "Crystalline Si-based in-plane tunable Fabry-Perot filter with wide tunable range," *IEEE/LEOS International Conference on Optical MEMS and Their Applications*, 2003, pp. 77-78.
Lipson et al., "Free-space MEMS tunable optical filter on (110) silicon", IEEE/LEOS *International Conference on Optical MEMS and Their Applications*, Oulu, Finland, 2005, pp. 73-74.
Saadany et al., "Electrostatically-tuned Optical Filter Based on Silicon Bragg Reflectors", in *IEEE/LEOS International Conference on Optical MEMS and Their Applications*, Big Sky, Montana, 2006, pp. 86-87.
Pruessner et al., "Integrated waveguide Fabry-Perot microcavities with silicon/air Bragg mirrors", *Optics Letters*, vol. 32, No. 5, Mar. 1, 2007, pp. 533-535.

(Continued)

*Primary Examiner* — Tri T Ton
(74) *Attorney, Agent, or Firm* — Fay Kaplun & Marcin, LLP

(57) ABSTRACT

A method for fabricating a tunable Fabry-Perot cavity comprises etching a substrate to form two reflectors separated by an air gap and an electrostatic mechanism. One of the two reflectors is mobile and connected to the electrostatic mechanism. Therefore, operation of the electrostatic mechanism moves the mobile reflector to change the thickness of the air gap and thereby tune the Fabry-Perot cavity. A tunable Fabry-Perot cavity fabricated with the above method comprises: a substrate; two reflectors formed in the substrate and separated by an air gap having a thickness, wherein one of the two reflectors is mobile; and an electrostatic mechanism formed in the substrate and connected to the mobile reflector. The mobile reflector connected to the electrostatic mechanism is moved upon operation of the electrostatic mechanism to change the thickness of the air gap and thereby tune the Fabry-Perot cavity. Applications of the Fabry-Perot cavity may comprise a tunable doped fiber laser, a tunable dispersion compensator and an integrated microfluidic refractometer.

5 Claims, 19 Drawing Sheets

OTHER PUBLICATIONS

Peter et al., "Tunable micro-electromechanical grating in silicon," *SPIE Optomechatronic Micro/Nano Devices and Components II*, Optics East 2006, Boston, Massachusetts, vol. 6376, paper 04, SPIE, 9 sheets.

Tormen et al., "Deformable MEMS grating for wide tunability and high operating speed," *Journal of Optics A*, vol. 8, No. 7, 2006., pp. S337-S340.

Digonnet et al., Rare-Earth-Doped Fiber Lasers and Amplifiers, Marcel Dekker, 2001, pp. 1-762.

Yamashita et al., "Widely Tunable Erbium-Doped Fiber Ring Laser Covering Both C-Band and L-Band," *IEEE J. Select. Topics Quantum Electron.*, vol. 7, No. 1, Feb. 2001, pp. 41-43.

Hunt et al., "Optofluidic integration for microanalysis", *Microfluidics and Nanofluidics*, vol. 4, No. 1, 2008, pp. 53-79.

Song, et al., "Refractive index measurement of single living cells using on-chip Fabry-Perot cavity", *Applied Physics Letters*, vol. 89, 2006, pp. 203-901.

Shao, et al., "Optofluidic intracavity spectroscopy of canine lymphoma and lymphocytes," *Photonics Technology Letters, IEEE*, vol. 20, No. 7, Apr. 7, 2008, pp. 493-495.

Masson, et al., "MEMS tunable silicon Fabry-Perot cavity," *Proceedings of SPIE*, vol. 6717, 2007, pp. 671-705.

Lipson et al., "Low loss 1D photonic band gap filter in (110) silicon," *Opt. Lett*, vol. 31, No. 3, Feb. 1, 2008, pp. 395-397.

Domachuk et al., "Compact Resonant Integrated Microfluidic Refractometer," *Applied Physics Letters*, vol. 88, 2006, p. 093513.

Shao et al., "Fabrication of a Fabry-Pérot cavity in a microfluide channel using thermocompressive gold bonding of glass substrates," *Journal of Microelectromechanical Systems*, vol. 14, No. 4, Aug. 2005, pp. 756-762.

\* cited by examiner operation 200 operation 202 operation 204 operation 206 operation 208 operation 210 operation 212

MEMS TUNABLE SILICON FABRY-PEROT CAVITY AND APPLICATIONS THEREOF

PRIORITY CLAIM

This application claims the benefit of U.S. Provisional Patent Application Ser. No. 60/935,417 filed on Aug. 10, 2007, the specification of which is expressly incorporated herein, in its entirety, by reference.

FIELD

The present invention is concerned with a tunable Fabry-Perot (FP) cavity and a method for fabricating this tunable FP cavity. The tunable FP cavity is micro-machined in a substrate, for example a silicon substrate. Also, the tunable FP cavity is actuated by an electrostatic mechanism. The present invention is also concerned with a tunable doped fiber laser, a tunable dispersion compensator, an integrated microfluidic refractometer and an optical attenuator using the tunable FP cavity.

BACKGROUND

One dimensional silicon photonic crystals are of great interest for several optical applications, such as in telecommunications and biochemical sensing, for example in measurements of the refractive index of gases and liquids. These crystals (a) are made of alternate layers of air and micro-machined silicon, (b) can be actuated in view of tuning their optical properties and (c) are fabricated by conventional silicon micro-machining processes. Several designs have been proposed but none of them provide a fast and wide tuning range, an easy fabrication process, low losses and a passive fiber alignment [1-4].

For example, tunable silicon optical filters using deformable Bragg gratings or tunable FP cavities have been proposed in Reference [2] and demonstrated in References [1, 6]. Such tunable FP filters can be used for a variety of applications such as optical filtering in telecommunications, biochemical sensing and tunable lasers. Tunable fiber lasers using intracavity fiber FP filters have also been previously reported in Reference [8]. However, none of them provide a fast and wide tuning range, an easy fabrication process, low losses and a passive fiber alignment [1-4].

SUMMARY

More specifically, in accordance with a first aspect of the present invention, there is provided a method for fabricating a tunable Fabry-Perot cavity, which comprises etching a substrate. Etching the substrate comprises: forming two reflectors separated by an air gap having a thickness, wherein one of the two reflectors is mobile on the substrate; and forming an electrostatic mechanism connected to the mobile reflector; wherein the mobile reflector connected to the electrostatic mechanism is moveable under the operation of the electrostatic mechanism so as to change the thickness of the air gap and thereby tune the Fabry-Perot cavity.

According to a second aspect of the present invention, there is provided a method for tuning a Fabry-Perot cavity having two reflectors formed into a substrate and separated by an air gap having a thickness, wherein one of the two reflectors is mobile. The method comprises: forming an electrostatic mechanism in the substrate; connecting the electrostatic mechanism to the mobile reflector; and operating the electrostatic mechanism to move the mobile reflector connected thereto; wherein moving the mobile reflector connected to the electrostatic mechanism changes the thickness of the air gap and thereby tune the Fabry-Perot cavity.

According to a third aspect of the present invention, there is provided a tunable Fabry-Perot cavity, which comprises: a substrate; two reflectors formed in the substrate and separated by an air gap having a thickness, wherein one of the two reflectors is mobile; and an electrostatic mechanism formed in the substrate and connected to the mobile reflector; wherein the mobile reflector connected to the electrostatic mechanism is moved upon operation of the electrostatic mechanism to change the thickness of the air gap and thereby tune the Fabry-Perot cavity.

According to a fourth aspect of the present invention, there is provided a tunable doped fiber laser, for generating laser at different wavelengths. The tunable doped fiber laser comprises: a laser source; a doped fiber connected to the laser source; and a tunable Fabry-Perot cavity, as described hereinabove, connected to the doped fiber; wherein tuning the tunable Fabry-Perot cavity allows for selecting different laser wavelengths.

According to a fifth aspect of the present invention, there is provided a tunable dispersion compensator for adjusting a group delay experienced by light when propagating through an optical fiber. The tunable dispersion compensator comprises: a tunable Gires-Tournois cavity comprising two reflectors separated by an air gap, wherein one of the two reflectors is mobile and a mechanism is connected to the mobile reflector to move the mobile reflector; and a waveguide positioned between the two reflectors; wherein moving the mobile reflector modulates a reflectivity of the tunable Gires-Tournois cavity and thereby adjust the group delay.

According to a sixth aspect of the present invention, there is provided an integrated microfluidic refractometer for measuring a refractive index of a fluid including at least one of a liquid and a gas. The refractometer comprises: a Fabry-Perot cavity; and a microfluidic channel, connected to the Fabry-Perot cavity, for carrying the fluid to the Fabry-Perot cavity; wherein the Fabry-Perot cavity detects a shift of wavelength corresponding to a variation of the refractive index when the fluid passes through the Fabry-Perot cavity.

According to a seventh aspect of the present invention, there is provided an optical attenuator for attenuating light transmission, comprising: a substrate; two reflectors formed in the substrate and separated by an air gap, wherein one of the two reflectors comprises an inner wall, a central wall and an outer wall separated from each other by other air gaps having respective thicknesses, and wherein the central wall is mobile; and an electrostatic mechanism formed in the substrate and connected to the mobile wall; wherein the mobile wall connected to the electrostatic mechanism is moved upon operation of the electrostatic mechanism to change the thicknesses of said other air gaps and thereby change reflectivity in the optical attenuator and attenuate light transmission through the optical the attenuator.

The foregoing and other objects, advantages and features of the present invention will become more apparent upon reading of the following non restrictive description of embodiments thereof, given by way of example only with reference to the accompanying drawings.

DETAILED DESCRIPTION

The following non-restrictive description of embodiments of the present invention is concerned with a tunable Fabry-Perot (FP) cavity micro-machined in, for example, silicon as a Micro-Electro-Mechanical System (MEMS) to form a FP filter. Two (2) Bragg reflectors form the two (2) mirrors of the FP cavity, the mirrors being separated from each other by an air gap. Tuning the thickness of the air gap between the mirrors, which in turn tunes the FP cavity, is performed through the use of an electrostatic comb drive actuator. The electrostatic comb drive actuator includes one comb drive supported by a set of springs, for example four (4) springs, to achieve a uniform modulation of the thickness of the air gap. Of course, a number of springs different from four (4) can be used.

For example, a voltage as low as 48.5V can be used to tune the FP cavity over a 100 nm bandwidth (covering more than the whole C-band) with a Full Width at Half Maximum (FWHM) varying from 4.4 to 7.6 nm. Transmission losses as low as −9.5 dB can be obtained.

The high aspect ratio etching of silicon enables the fabrication of small size features simultaneously with the fabrication of optical fiber alignment grooves used in passive alignment of optical fibers. The in-plane design also facilitates passive fiber alignment. Spring fiber holders can be also fabricated in the grooves to obtain perfect alignment.

The FP filters find applications in telecommunications, bio-sensing, and tunable lasers. For example, lasers using an Erbium-doped fiber can be tuned over a large bandwidth since the Erbium gain spans over the C- and L-bands. The C-band has a range of wavelength from 1530 nm to 1565 nm, and the L-band has a wavelength range between 1565 nm and 1625 nm.

Also, inserting a tunable FP filter inside a fiber laser cavity makes possible the construction of a high power tunable laser suitable for the replacement of many laser sources in telecommunication systems.

In the following description, the basic theory for designing filters using the optical behavior of Bragg gratings and FP cavities will be first summarized. Then, a process for fabricating such FP cavities will be described. The FP cavities fabricated using this process will be characterized both optically and electrostatically. Finally, applications using the fabricated FP cavities will be disclosed. These applications may comprise a tunable doped fiber laser, a refractometer for microfluidic systems, a tunable dispersion compensator, etc.

1. Theory

Figure 1:
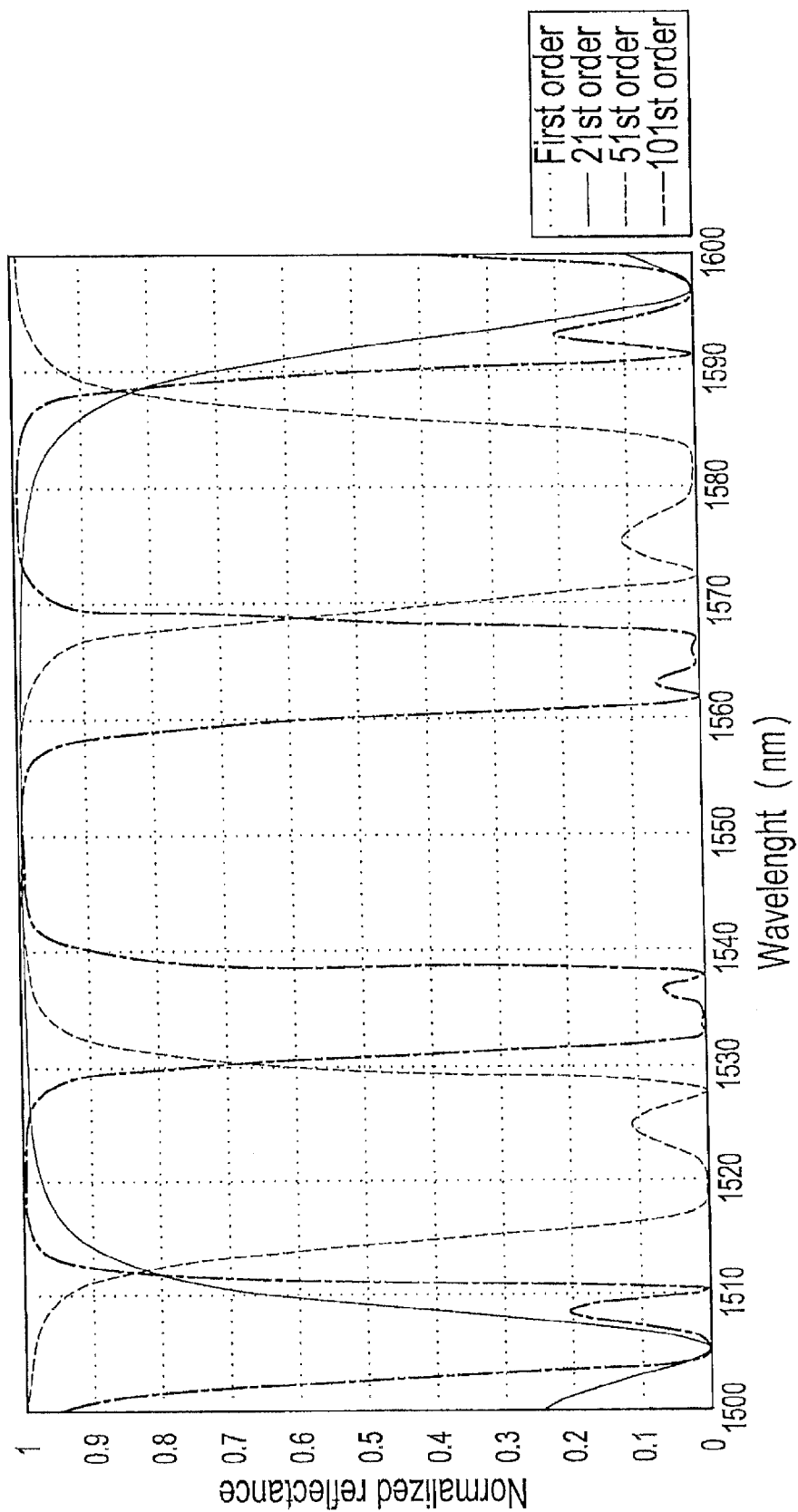
FIG. 1 is a graph of normalized reflectance versus wavelength for a three-layer grating used as a reflector with four (4) different orders of the silicon layers: $1^{st}$, $21^{st}$, $51^{st}$ and $101^{st}$.

The transfer matrix method can be used to simulate reflected and transmitted light at wavelength λ across a FP cavity [5]. Each layer of silicon and air has its own respective characteristic matrix. Bragg reflectors, forming the mirrors of the FP cavity, will be first considered. The relation between the wavelength λ and the thickness of each layer is as follows:

$$\Lambda = \frac{N\lambda}{4n} \quad (1)$$

where Λ represents the thickness of the layer, n represents the refractive index of the layer, λ represents the wavelength of the light and N represents the order of the silicon or air layer. The order of the silicon layer is related to the thickness of the layer. For example, for each layer of the Bragg mirror, in order to obtain a high reflectivity, an odd integer representing the order of the layer should be calculated, according to Equation (1). As an example, with a refractive index of silicon $n_{Si}$=3.45 and a refractive index of air $n_{air}$=1 at a wavelength λ=1550 nm, the thickness of a layer of silicon is given by $\Lambda_{Si}$=112 nm and the thickness of a layer of air is given by $\Lambda_{air}$=388 nm at the first order (N=1) of the silicon or air layer. The thickness can also be a multiple of higher orders (2m+1)Λ, where N=(2m+1) and m is an integer. In this example, the Bragg reflectors will present a wide reflection bandwidth for use as the mirrors of the FP cavity. More specifically, a wide reflection bandwidth of the Bragg mirrors will provide a wide tuning range of the FP cavity. The transmission peak of the resulting FP filter will occur within the reflection bandwidth of the Bragg mirrors. The orders of the air and silicon layers are elements to be considered in achieving the wide bandwidth objective. FIG. 1 shows the relationship between the order of the silicon layers and the reflection peak bandwidth of one Bragg reflector. As the order of the silicon layers decreases, the reflection peak bandwidth gets larger. The first order is barely visible since it is almost a straight line at the reflectance value of 1.

Figure 2:
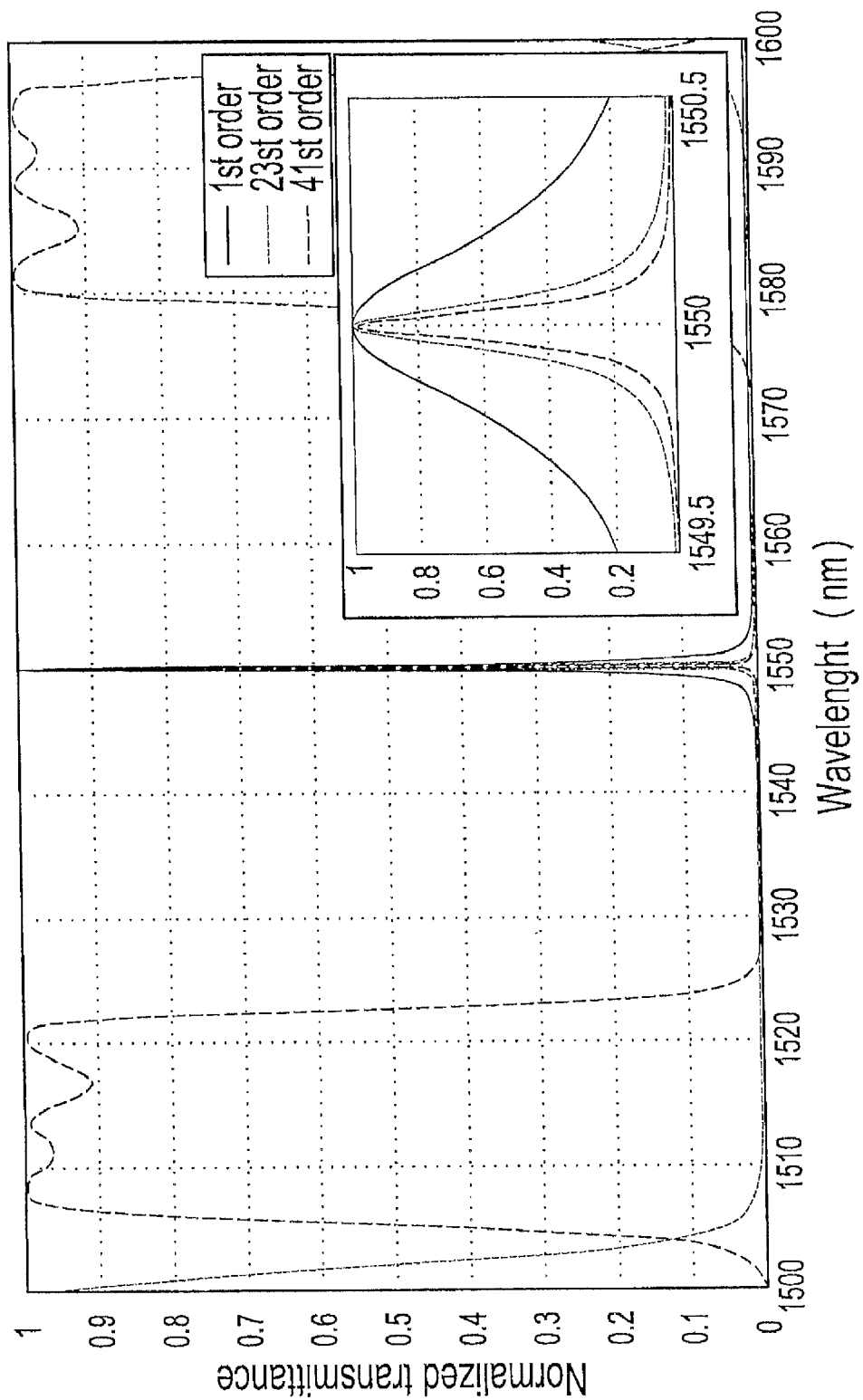
FIG. 2 is a graph of normalized transmittance versus wavelength for a FP cavity according to one embodiment of the present invention, with two three-layer gratings used as reflectors and an air gap, wherein an inset shows a close up view of the peaks for three (3) different orders of the silicon layers: $1^{st}$, $23^{rd}$ and $41^{st}$.

To make a FP cavity, a minimum of two Bragg reflectors separated by an air gap of thickness:

$$\Lambda_{FP} = \frac{k\lambda}{2} \quad (2)$$

can be used, where k is the order of the air gap of the FP cavity. FIG. 2 shows that a higher order of the silicon layers improves the finesse of the FP filter, but decreases the stopband, thus limiting the tuning range. A FP cavity with an order of the silicon layers around 23 seems to be a good compromise between the tuning range, finesse, and the thickness of the silicon walls for ease of fabrication. The number of walls of the Bragg reflectors has an impact on the reflectivity of these Bragg reflectors: the higher the number of walls, the higher the reflection and thus the better the finesse of the FP cavity. But in practice, since the fabrication process generates deviations on the geometry of the walls, increasing the number of walls will also increase the losses. In fact, the walls are not perfectly vertical due to the deep etching process. Adding more walls will increase losses since the light will experience multiple reflections on each layer of the reflector. It was found experimentally that the optimal number of walls is three.

2. Fabrication

A FP cavity according to one embodiment of the present invention is fabricated by silicon micro-machining. For example, the FP cavity and optical fiber alignment grooves can be fabricated through a single etching process, for example one single operation of Deep Reactive Ion Etching (DRIE) on a Silicon On Insulator (SOI) wafer. The SOI wafer may comprise a 70 μm thick cavity-forming silicon (Si) layer. Although a cavity-forming silicon (Si) layer having a thickness of 70 μm can be used, the thickness of this cavity-forming silicon (Si) layer can be increased, for example to 85 μm, to further reduce losses. Of course, it is within the scope of the present invention to use another type of etching process.

Figure 3A:
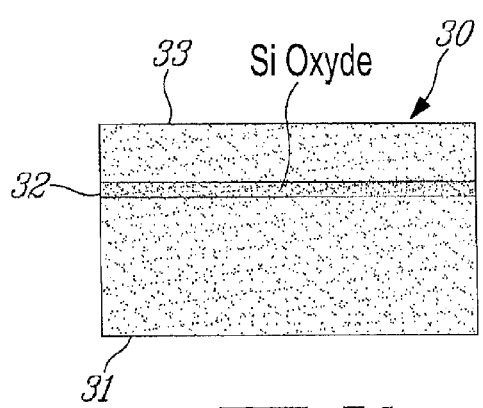
FIGS. 3a)-3d) are schematic views of operations conducted during micro-machining of one embodiment of the tunable FP cavity, wherein FIG. 3a) is a side elevational view of a wafer with a 70 μm thick cavity-forming layer, FIG. 3b) is the same side elevational view showing photolithography of a 4 μm thick resist layer, FIG. 3c) is the same side elevational view illustrating vertical etching of the 70 μm thick cavity-forming layer and FIG. 3d) is the same side elevational view illustrating the FP cavity released by etching silicon oxide in liquid hydrogen fluoride.

Turning now to FIGS. 3a)-3d), the process of fabricating a FP cavity 34 will be described.

FIG. 3a)

A multi-layer substrate, more specifically a SOI wafer 30 is used. The multi-layer substrate 30 comprises a bottom layer 31 made of Si, an intermediate 2 μm thick layer 32 of Si oxide placed on top of the Si layer 31, and finally a 70 μm thick cavity-forming Si layer 33 placed on top of the intermediate Si oxide layer 32. It is within the scope of the present invention to use layers of different thicknesses.

FIG. 3b)

A 4 μm thick masking layer 35 of SPR220 3.0 photoresist is applied on top of the Si layer 33. More specifically, this photoresist is a resin known as MEGAPOSIT® SPR®220 Series Photoresist commercialized by the Shipley Company, L.L.C., Marlborough, Mass., USA. Of course, it is within the scope of the present invention to use any other suitable photoresist. A thick masking layer is needed for the subsequent 70 μm DRIE operation. Also, it is possible to use different degrees of thickness of the masking layer 35.

Figure 3C:
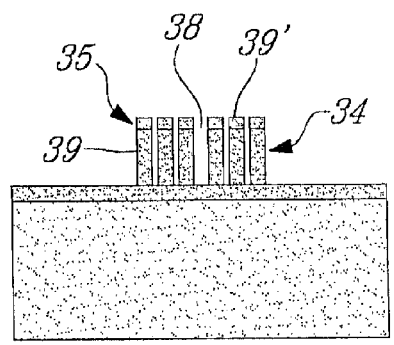
Figure 3B:
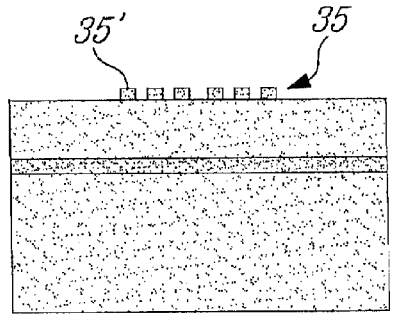

As illustrated in FIG. 3b) the 4 μm masking layer 35 is patterned to define a photoresist mask 35' shaped and dimensioned to form the FP cavity 34 through the subsequent DRIE operation.

Various processes can be used to apply the masking layer 35 on top of the Si layer 33 and produce the mask 35' including, amongst other, spin coating and photolithography. Such processes are believed to be well known to those of ordinary skill in the art and, accordingly, will not be further described in the present specification.

FIG. 3c)

FIG. 3c) schematically shows the structure of the FP cavity 34 produced using an Inductively Coupled Plasma (ICP) DRIE operation performed in connection with the masking layer 35 and corresponding mask 35'. As shown in FIG. 3c), the DRIE operation is performed through the 70 μm thickness of the cavity-forming Si layer 33. Of course, it is within the scope of the present invention to use any other alternative type of etching process.

More specifically, the structure of the FP cavity 34 comprise, in the example of FIG. 3c), two (2) sets of three (3) vertical walls 39 and 39' separated by an air gap 38. In each set, the vertical walls 39, 39' are equally spaced apart from each other. The two (2) sets of three (3) vertical walls 39 and 39' form respective Bragg reflectors (Bragg gratings).

Precise verticality of the etched structures, including the walls 39 and 39', of the FP cavity 34 will lower the optical losses of the FP cavity 34. For that purpose, a 450 W forward ICP power and a 25 W RF power can be used for the etching operation, and 450 W forward ICP power and 10 W RF power can be used for the subsequent passivation operation. The etching process is performed at a pressure of, for example, 15 mTorr. The pressure is a factor to consider in the control of the sidewall profile. Furthermore, smoothness of the walls 39 and 39' can be improved by adding oxygen during the etching operation.

FIG. 3d)

The intermediate 2 μm buried Si oxide layer 32 and the masking layer 35 are etched away, for example in liquid Hydrogen Fluoride (HF) to release the FP cavity 34. An operation of $CO_2$ drying is then performed in order to prevent the structures of the FP cavity 34 from sticking.

Figure 3D:
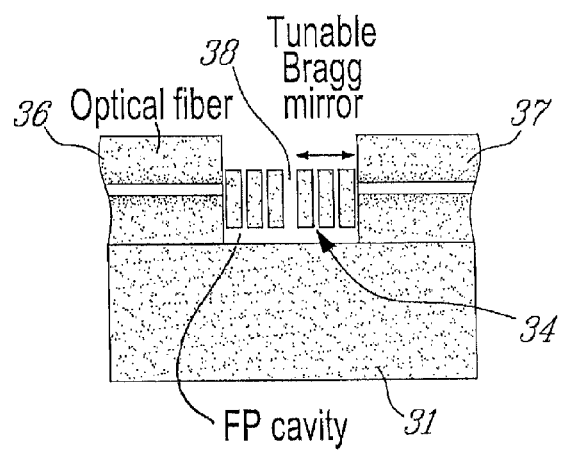

Two optical fibers 36 and 37 are respectively placed on opposite sides of the FP cavity 34. The optical fibers 36 and 37 can be passively aligned using deep silicon square grooves (not shown in FIG. 3d) formed, for example, in the Si layer 33 along with the FP cavity 34 during the etching process. For example, 125 μm diameter single mode fibers (Corning SMF-28e) can be used so that the top of the fiber core is 5.4 μm lower than the top of the Bragg reflectors (Bragg gratings) to insure a good coupling between the single mode fibers and the Bragg reflectors (Bragg gratings).

Figure 4:
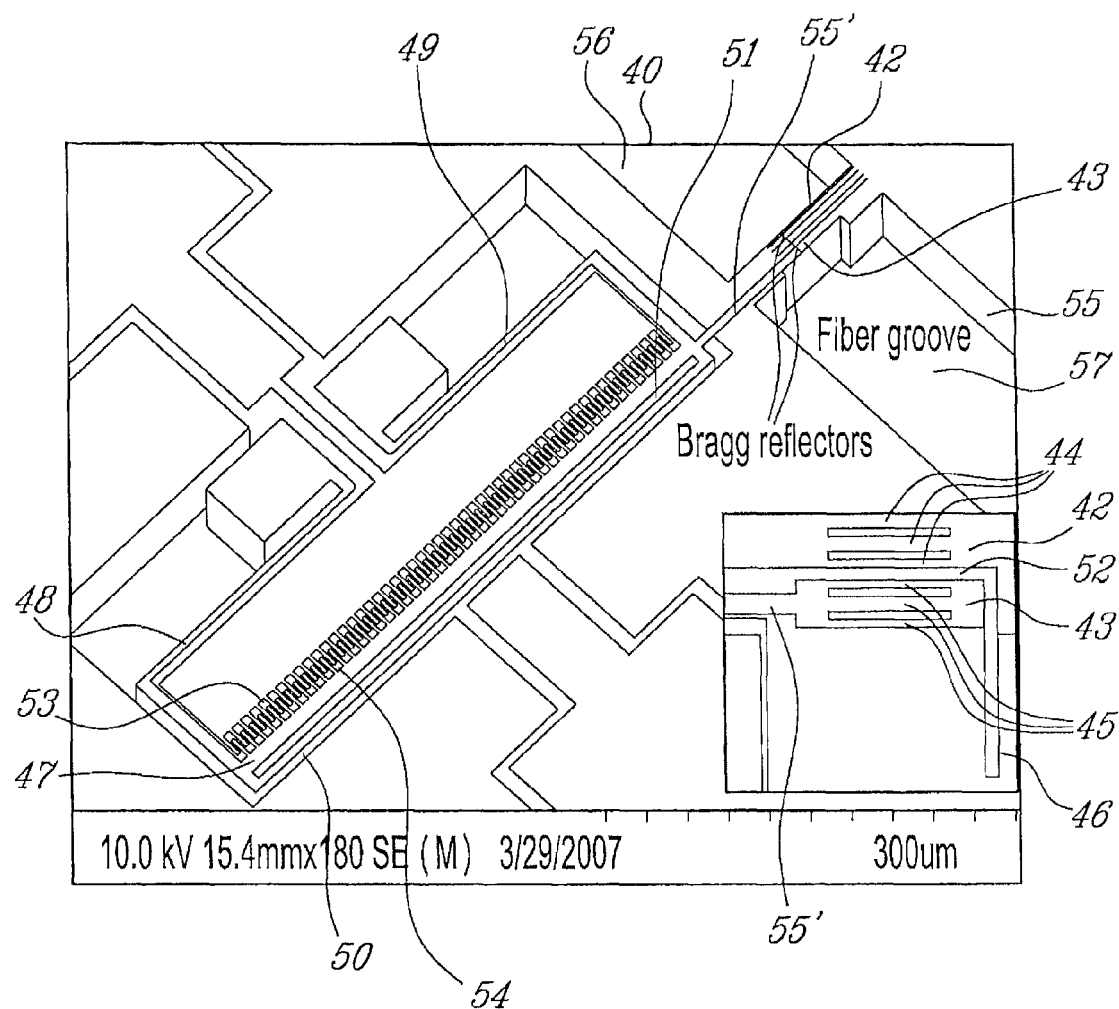
FIG. 4 is a SEM (Scanning Electron Micrograph) photograph of a silicon micro-fabricated FP cavity in which the inset is an enlarged view of two Bragg mirrors forming part of the FP cavity.

FIG. 4 is a Scanning Electron Micrograph (SEM) of a FP cavity 40 fabricated using the above described fabrication process. The FP cavity 40 comprises two (2) Bragg reflectors 42 and 43, each of them made of three (3) silicon walls 44 and 45, respectively (see inset 46 of FIG. 4). The Bragg reflector 42 is stationary or fixed with respect to the multi-layer substrate 30 (FIGS. 3a)-3d)) while the Bragg reflector 43 is mobile about the same substrate 30. The FP cavity 40 further comprises an air gap 52 between the two (2) Bragg reflectors 42 and 43.

Etched in the Si layer 33 (FIGS. 3a)-3b)) during the same etching operation as described herein above to produce the FP cavity 40 is an electrostatic mechanism, more specifically a comb drive actuator comprising a comb 53 stationary or fixed with respect to the multi-layer substrate 30, and a comb drive 47 which is mobile with respect to the same substrate 30. To make the comb 53 stationary or fixed with respect to the multi-layer substrate 30, the intermediate 2 μm thick layer 32 of Si oxide may not be removed under this comb 53 by the liquid Hydrogen Fluoride (HF) etching process. The same is valid for other portions of the system of FIG. 4 that need to be stationary or fixed with respect to the multi-layer substrate 30.

The comb drive 47 comprises a comb 54 imbricated with the fixed comb 53. The comb drive 47 is connected to the mobile Bragg reflector 43 through an arm 55'. The comb drive 47 is suspended from the multi-layer substrate 30 by and therefore movable with respect to the substrate 30 through a set of four springs 48-51 to provide through the arm 55' a uniform modulation of the thickness of the air gap 52 of the FP cavity 40 between the Bragg reflectors 42 and 43. A number of springs different from four (4) can obviously be used.

Applying a voltage difference between the two combs 53 and 54 will make the combs 53 and 54 to move closer to each other so as to reduce the thickness of the air gap 52 of the FP cavity 40. Reducing the thickness of the air gap 52 reduces the filtered wavelength.

It should be also mentioned that the vertical roughness of one silicon wall, such as 44 or 45, of a Bragg reflector, such as 43, has been measured with an Atomic Force Microscope (AFM) to yield 26.2 nm rms. Verticality was estimated on a SEM to be less than 0.5°.

3. Results

In this section, the behavior of a Bragg reflector (Bragg grating) used as a mirror in the FP cavity 34 of FIG. 3 or the FP cavity 40 of FIG. 4 will be described. Then, the FP cavity 40 will be presented. Finally, the effect of tuning the thickness of the air gap 52 of the silicon FP cavity 40 will be demonstrated.

3.1 Bragg Gratings

Figure 5:
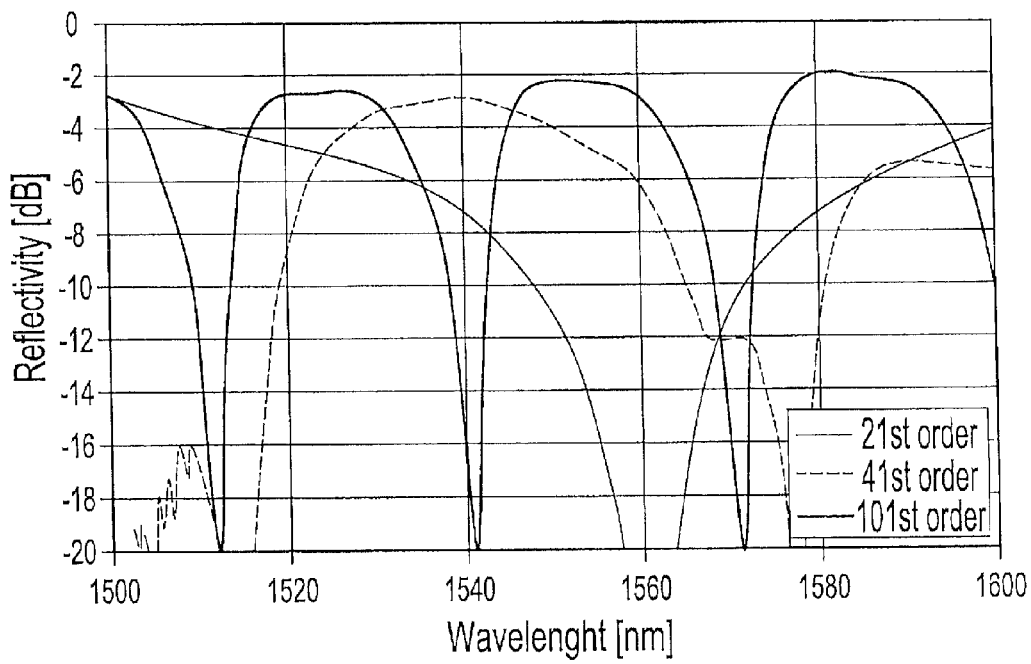
FIG. 5 is a graph of reflectivity versus wavelength for three (3) Bragg mirrors structures with $21^{st}$, $41^{st}$ and $101^{st}$ orders of the silicon layers, respectively.

It was experimentally observed that the reflection bandwidth decreases as the order of the silicon layers increases as predicted in the foregoing description. FIG. 5 shows three different experimental reflection spectra for the $21^{st}$, $41^{st}$ and $101^{st}$ orders of the silicon layers. It can be seen that the number of reflection peaks increases with higher orders.

Figure 6:
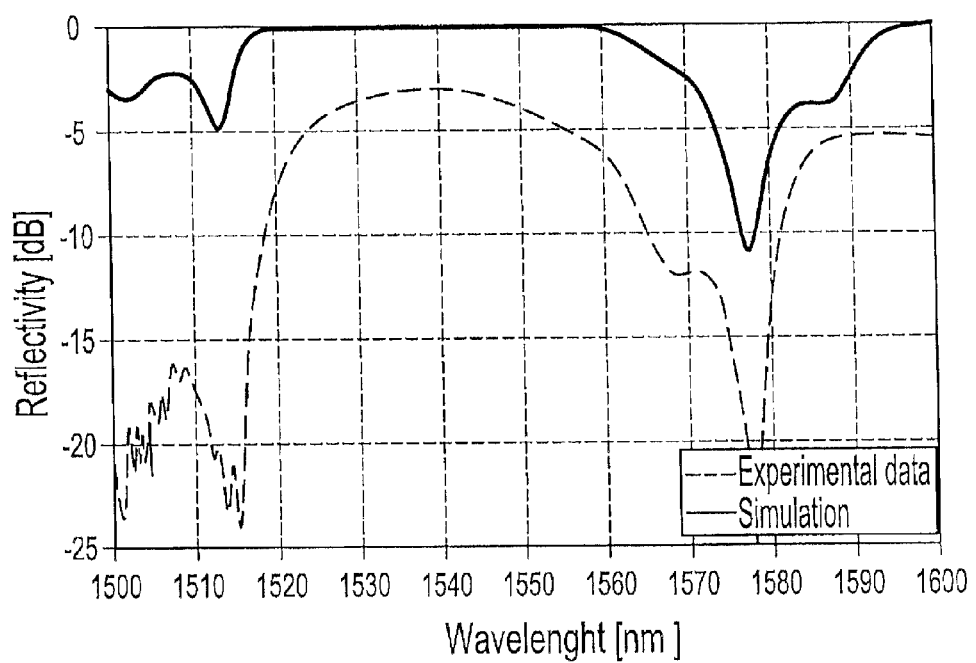
FIG. 6 is a graph of simulated (plain line) and measured (dotted line) reflectivity versus wavelength for a Bragg reflector with a $41^{st}$ order of the silicon layers, $11^{th}$ order of the air layers and three silicon walls.

FIG. 6 shows the reflection spectrum of a fabricated Bragg reflector obtained through experimental data and the reflection spectrum of a corresponding simulated Bragg reflector. The overall behaviors of the two spectra are very similar. Since reflection losses were not considered in the simulation, the experimental data present higher reflection losses compared to the simulation. The reflection losses are mainly due to verticality deviations of the silicon walls 44, 45 of the Bragg reflector 42, 43 and to scattering. Other imperfections were introduced by the fabrication process. In particular, the silicon walls 44, 45 were thinner than expected because of the DRIE process. The real dimensions of the Bragg grating were different from the ideal ones calculated through Equation (1) and therefore the real spectra were different from the ideal ones shown in FIG. 1. A deviation of the wall thickness generates a larger or smaller bandwidth and causes the reflection and transmission peaks to shift wavelength.

3.2 Fabry-Perot

Figure 7:
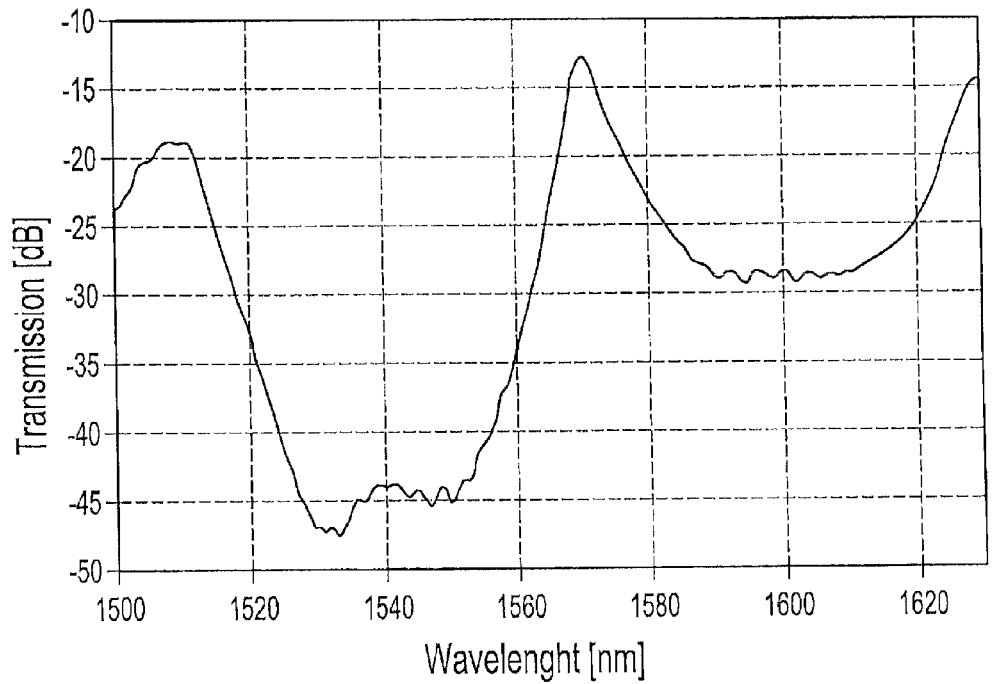
FIG. 7 is a graph of an experimental transmission spectrum for a micro-fabricated silicon FP cavity according to one embodiment of the present invention.

First, fixed FP filters will be considered. The transmission spectrum of the fixed FP filters has a typical band-pass behavior as illustrated in FIG. 7. The transmission loss of fixed FP filters is −11 dB, which is comparable to previously reported silicon filters [2-3] and the isolation is −20 dB. The bandwidth at −3 dB is 14 nm.

Figure 8:
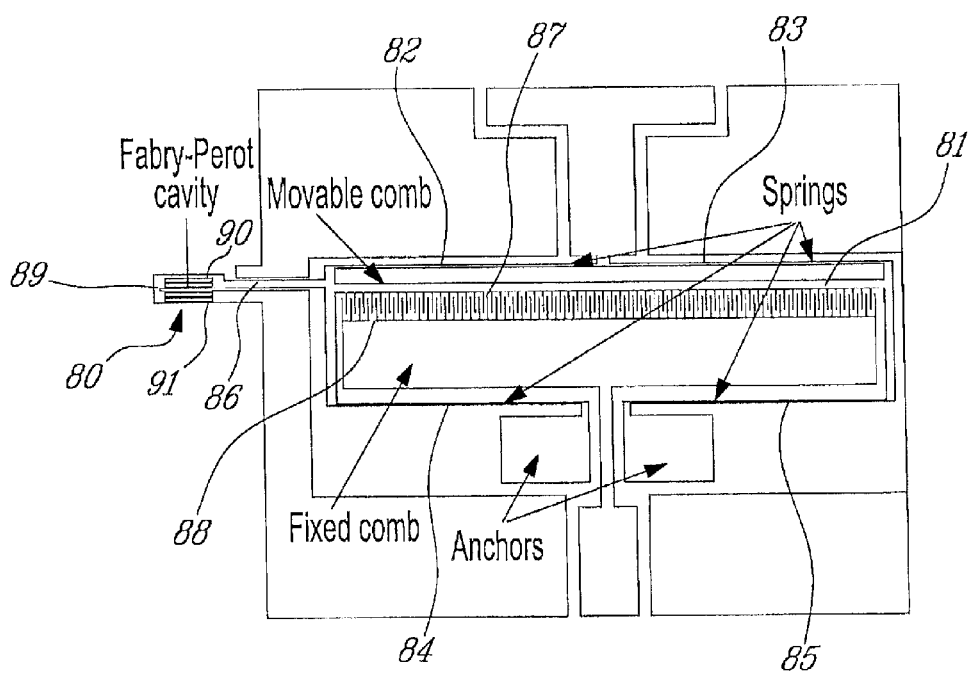
FIG. 8 is a schematic view of a FP cavity according to one embodiment of the present invention, including a comb drive actuator and a four-spring mechanism.

Turning now to the schematic diagram of FIG. 8, a tunable FP cavity 80 can be actuated using an electrostatic mechanism. The tunable FP cavity 80 comprises a stationary or fixed Bragg reflector 91 and a mobile Bragg reflector 90 separated by an air gap 89. The electrostatic mechanism comprises a comb drive actuator provided with a fixed comb 88 and a mobile comb drive 81 suspended by four springs 82-85. The mobile comb drive 81 comprises a comb 87 and is connected to the mobile Bragg reflector 90 through an arm 86. The comb drive 81 produces a uniform displacement of the mobile Bragg reflector 90 by applying a low voltage difference between the combs 87 and 88. The uniform modulation of the thickness of the air gap 89 represents a significant improvement compared to the device of Lipson [2]. Indeed, a non-uniform modulation would generate an angle between the two Bragg reflectors 90 and 91, thus changing the resonance properties of the FP cavity 80. These changes can lead to a different filtered wavelength, limited tuning range or significant increase of transmission losses. Also, these changes can lead to an increase of full width at half maximum (FWHM) of the transmission peak.

Figure 9:
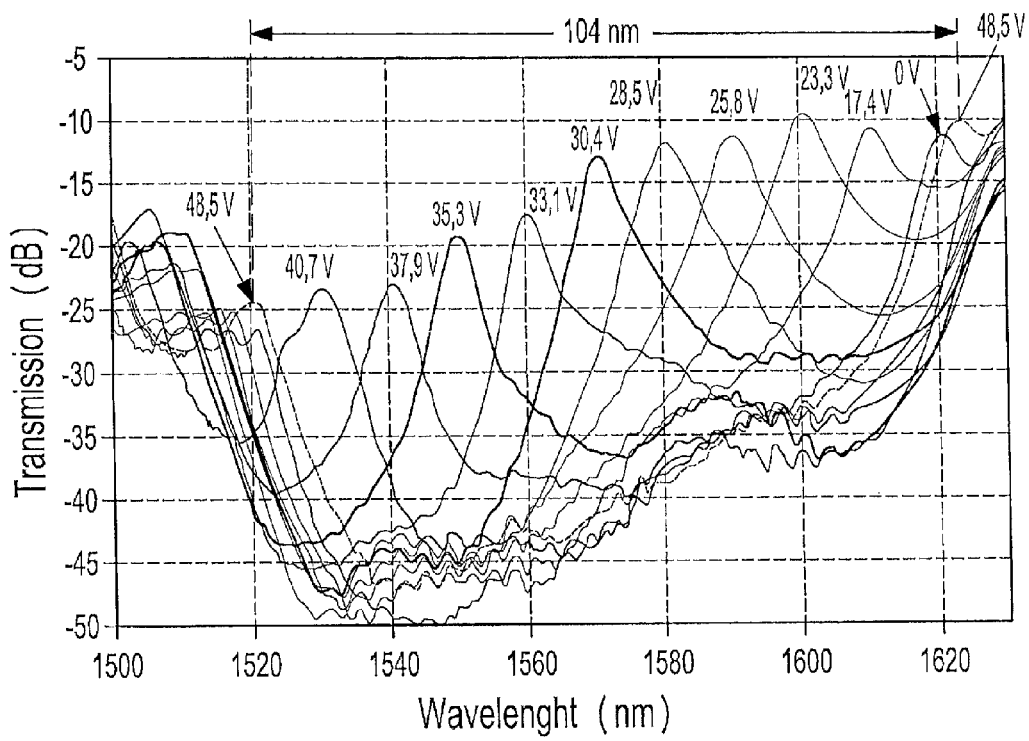
FIG. 9 is a graph of transmission spectra of the FP cavity of FIG. 8, tuned from 1621 nm down to 1520 nm, wherein the voltage applied to the comb drive actuator changes from 0V to 48.5V.

FIG. 9 shows the effect on the spectra of the tuning of the thickness of the air gap 89 of the FP cavity 80. In the example of FIG. 9, the initial transmission peak is 1621 nm. As the voltage between the two combs 87 and 88 increases, the thickness of the air gap 89 between the two Bragg reflectors 90 and 91 decreases. Thus, the transmission peak shifts towards smaller wavelengths. The FP cavity 80 can be tuned continuously down to 1520 nm for a total tuning range of 101 nm. The FWHM (Full Width at Half Minimum) varies from 4.4 to 7.6 nm. The maximum applied voltage (maximum tuning range of the FP cavity 80) is 48.5V.

Figure 10:
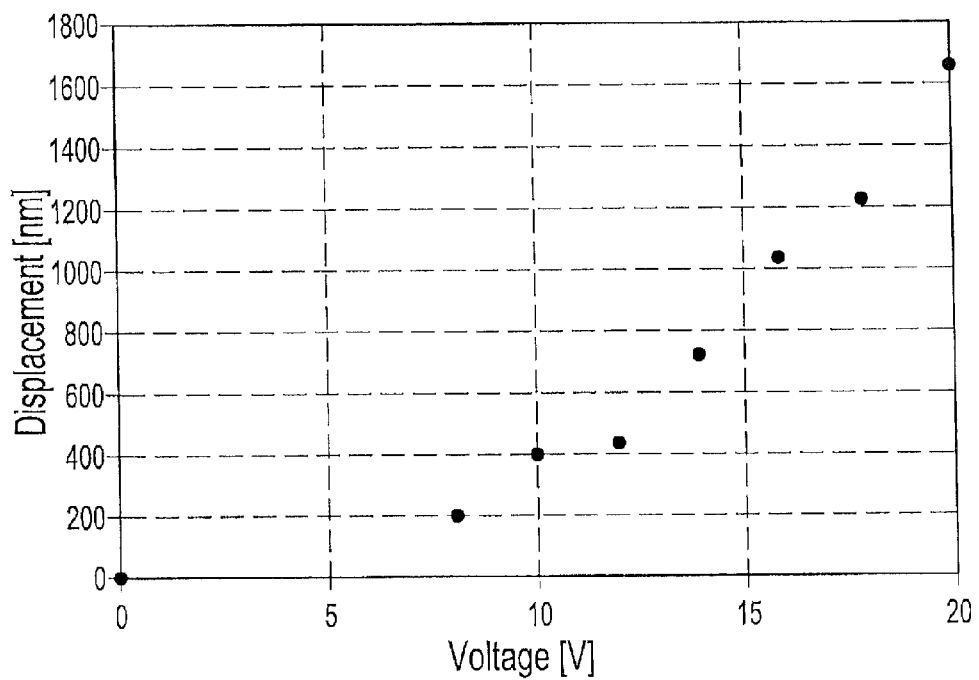
FIG. 10 is a graph of measured displacements of one Bragg mirror of the FP cavity of FIG. 8 versus applied voltage.

FIG. 10 characterizes the modulation of the air gap 89 of the FP filter 80 versus the applied voltage. The measurements were made by a dynamic white light interferometer (not shown). It can be seen that the maximum tuned wavelength is reached when the thickness of the air gap 89 is reduced by about 850 nm, corresponding to the maximum applied voltage of 15.4V.

4. Conclusion

The design of a continuously tunable Fabry-Perot cavity micro-machined in silicon has been presented in the foregoing description. A tunable FP filter in silicon that is fabricated in one single etch step has been demonstrated. The above described fabrication process produces wall roughness of 26.2 nm rms and verticality of less than 0.5°. Moreover, the modulation of the thickness of the air gap is made uniform using a comb drive and a set of four (4) springs. Measured optical characteristics are in good agreement with the predicted characteristics from the numerical simulations. The influence of the order of the silicon/air pair was demonstrated theoretically and experimentally. The tuning effect of the FP air gap is reported on a bandwidth as large as 101 nm, covering more than the whole C-band. The transmission losses are as low as −9.5 dB. The maximum actuation voltage required to cover the whole tuning bandwidth is as low as 48.5 V.

5. Applications

In this section, a plurality of examples of applications using, for example, the FP cavity 40 of FIG. 4 will be described.

5.1 Tunable Erbium Doped Fiber Laser Using a Silicon Micro-Electro-Mechanical Fabry-Perot Cavity A first example of application using a silicon MEMS Fabry-Perot cavity according to the present invention consists of a tunable Erbium-doped fiber laser.

With the development of Dense Wavelength Division Multiplexing (DWDM) networks, numerous laser sources emitting at different wavelengths are needed. The multiplication of laser sources has a large cost impact on DWDM networks. For that reason, a MEMS tunable Erbium-doped fiber laser, which could potentially replace several prior lasers at a reasonable cost, would be advantageous.

It should be noted that elements, other than Erbium, can be used to dope the fibers.

As the gain of Erbium spans over a large wavelength range centered at 1550 nm, the MEMS tunable Erbium-doped fiber laser using a Fabry-Perot cavity according to the present invention enables tuning over the whole C-band [7].

Figure 12:
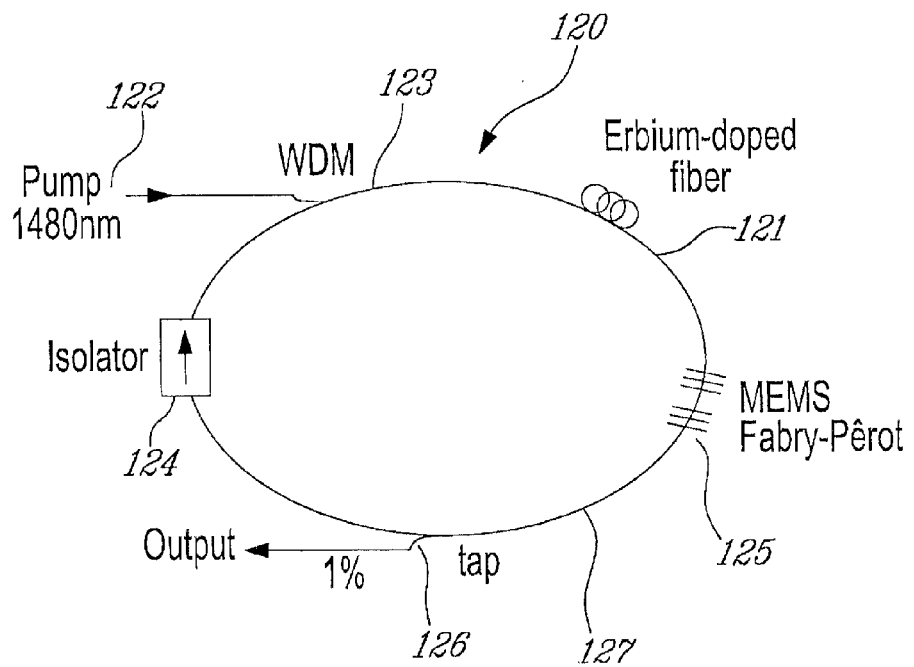
FIG. 12 is a schematic diagram of an optical setup of a ring fiber laser.
Figure 13:
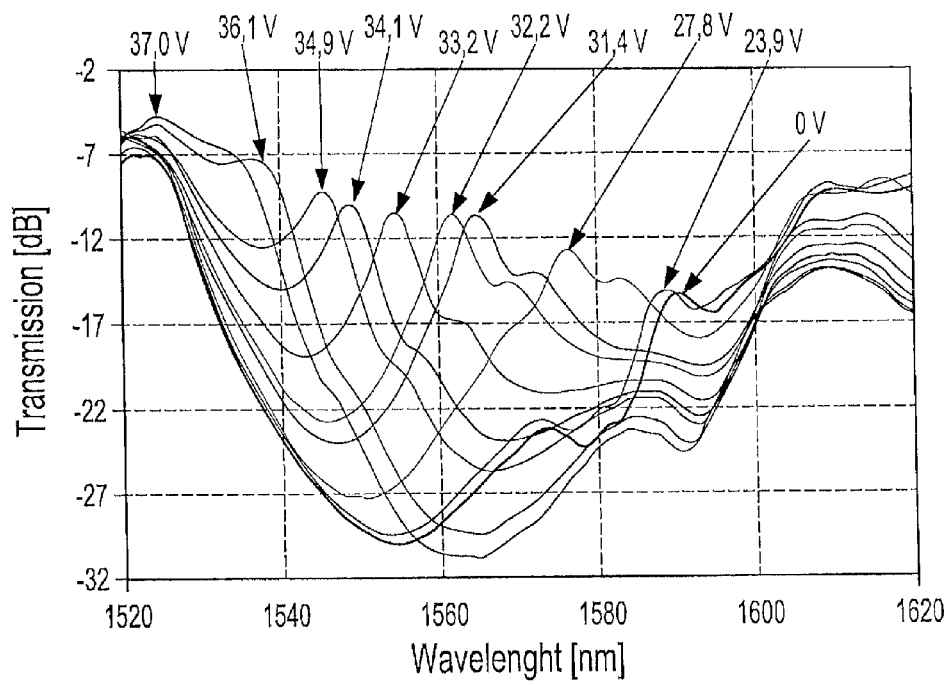
FIG. 13 is a graph of transmission spectra of a tuned FP cavity according to one embodiment of the present invention.

Now turning to FIG. 12, a setup of a ring laser 120 comprising a loop formed of an Erbium-doped optical fiber 121 and an output optical fiber 127 will be described. The Erbium-doped fiber 121 is pumped with a 1480 nm laser diode 122 through a 1480 nm/1550 nm Wavelength Division Multiplexer (WDM) coupler 123. An isolator 124 is used to insure one way lasing direction in the loop formed by the optical fibers 121 and 127. The ring laser 120 also includes a MEMS FP filter 125 such as, for example, the FP cavity 40 of FIG. 4. The MEMS FP filter 125 is positioned within a ring cavity to select the lasing wavelength. A 1% tap 126 is mounted on the output fiber 127 as an output coupler to minimize losses in the cavity of the FP filter 125.

Alignment of the optical fibers 121 and 127 with the MEMS FP filter 125 should be accurate. More specifically, the doped fiber 121 and the output fiber 127 are passively aligned by silicon fiber grooves, such as 56 and 57 in FIG. 4 on each side of the tunable FP filter 125, as described and illustrated for example in FIG. 3d) and FIG. 4.

As mentioned hereinabove, the MEMS FP filter 125 is formed by the FP cavity, such as 40 of FIG. 4. The mirrors of the FP cavity 40 are made of two (2) silicon Bragg reflectors 42 and 43. One 42 of these mirrors/reflectors is stationary or fixed, while the other one 43 is mobile and can be displaced by the comb drive 47. When a voltage is applied to the combs 53 and 54, the combs 53 and 54 get closer to each other and thus the thickness of the air gap 52 of the FP cavity 40 is tuned.

Figure 11:
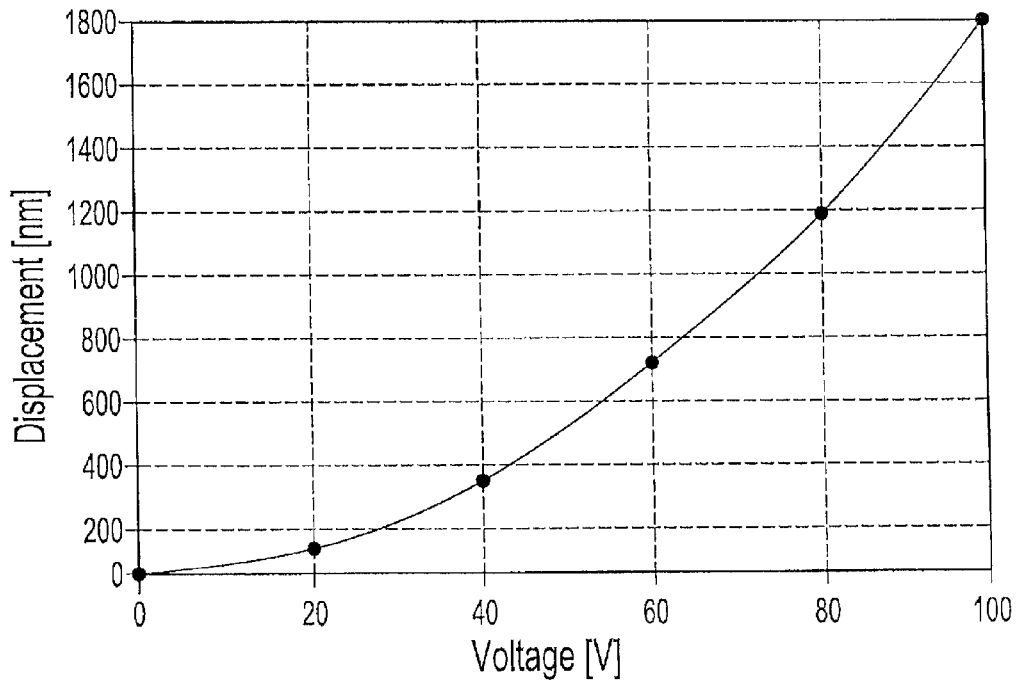
FIG. 11 is a graph showing simulation results of the displacement of the comb drive actuator versus applied voltage.

FIG. 11 is a graph of the simulated displacement of the comb drive 47 versus the voltage. When the combs 53 and 54 come closer, the thickness of the air gap 52 of the FP cavity 40 is decreased. A smaller air gap 52 means a shorter filtered wavelength by the FP cavity 40.

Figure 14:
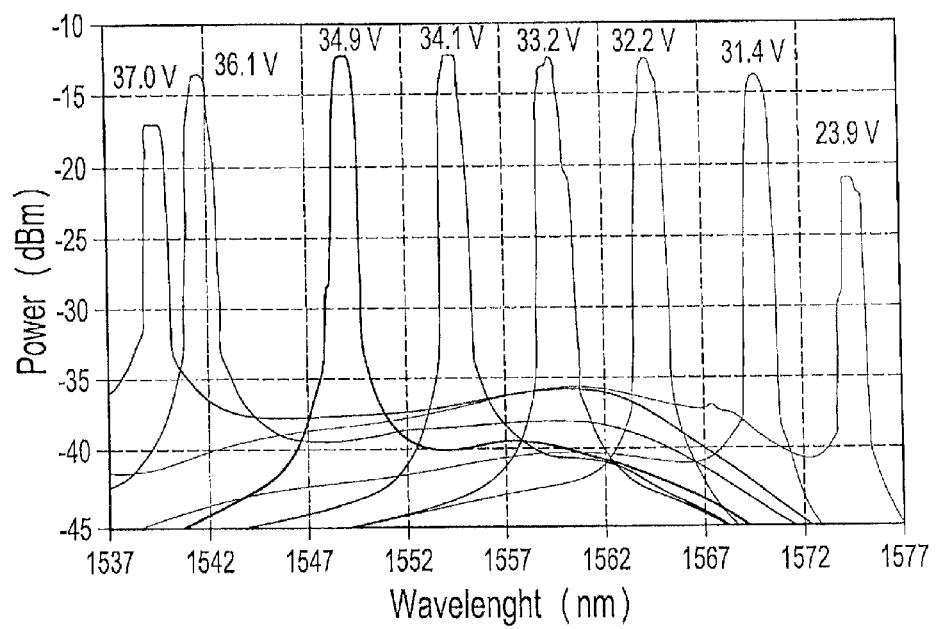
FIG. 14 is a graph of measured fiber laser spectra at different voltages applied to the comb drive actuator of the FP cavity.

The transmission peak of the FP filter shifts to a shorter wavelength while increasing the voltage applied to the combs 53 and 54 as shown in FIG. 14. The largest tuning of the FP filter 125 is reached at a voltage of 37V. A 35 nm tuning range of the fiber laser from 1574 nm to 1539 nm with increasing voltage applied to the combs 53 and 54 of FIG. 4 was measured. The spectral width of the fiber laser is approximately 0.1 nm (FWHM).

5.2 Tunable Dispersion Compensator Using a Silicon Micro-Electro-Mechanical Gires-Tournois Cavity A second example of application using the illustrative embodiment of the present invention is given by a tunable dispersion compensator.

Dispersion constitutes a common problem in guided optics using waveguides, such as optical fibers, since the latter provides for a dispersive environment. Indeed, dispersion is the phenomenon in which propagation of different wavelengths of a light beam is conducted with different speeds in a given medium.

In current telecommunication systems using optical fibers, fixed dispersion compensators are provided punctually along the transmission lines in order to compensate for the dispersion phenomenon in these optical fibers. Generally, at the two extremities of the transmission lines, tunable dispersion compensators are provided for compensating changes due to the environment surrounding the optical fibers such as the temperature variations, for example.

The current tunable dispersion compensators typically use thermal drivers for tuning purposes, which is both complex and slow. In contrast, the current tunable dispersion compensator using a silicon MEMS cavity according to the present invention allows for a simple and fast system. Indeed, the electrostatic comb drive 47 of FIG. 4 has an actuating velocity of $10^{-4}$ seconds compared to 10 seconds for the thermal actuator. Also, the fabrication process as illustrated in FIG. 3 allows for an easy and mass production.

Figure 15:
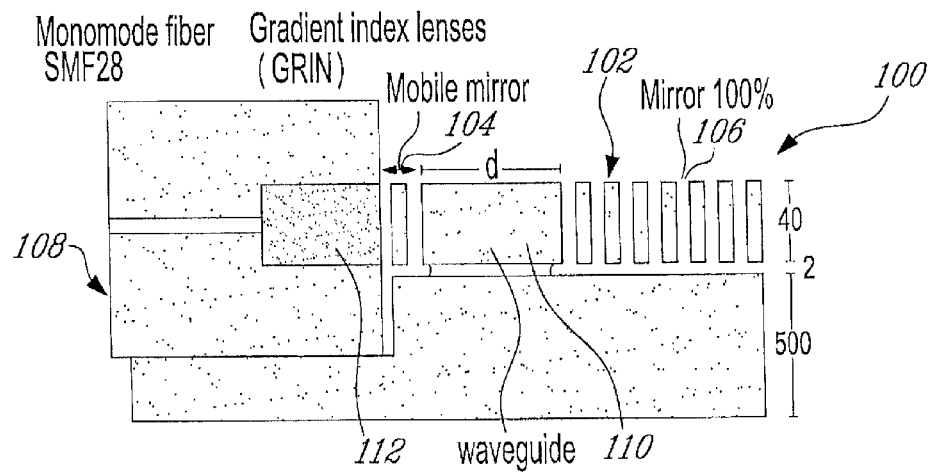
FIG. 15 is a schematic diagram of a tunable dispersion compensator using a FP cavity according to one embodiment of the present invention.

Turning now to FIG. 15, the tunable dispersion compensator 100 using a silicon MEMS cavity 102 will be described.

The MEMS cavity 102 comprises two mirrors 104 and 106. Those mirrors are composed of layers of air and silicon. The mirror 106 is designed in such a way as to obtain a reflection coefficient of about 100%. In this way, the incident light is returned to the input fiber 108, which can be a single mode fiber such as a SMF28 (Single-Mode optical Fiber 28). The mirror 104 is partially reflecting in order to allow the light to penetrate into the cavity 102 and to enter into resonance. The silicon layer of the mirror 104 can be moved so as to modulate the reflectivity of the mirror and the effective length of the cavity 102. More specifically, this allows for adjusting the group delay that is experienced by the light when it propagates through the tunable dispersion compensator 100.

It should be noted that more specifically in this configuration, the cavity 102 corresponds to a Gires-Tournois (GT) cavity.

Between the mirrors 104 and 106, a waveguide 110 of length d is positioned. Propagation of light through this waveguide 110 limits losses due to diffraction occurring during multiple reflections.

Figure 16:
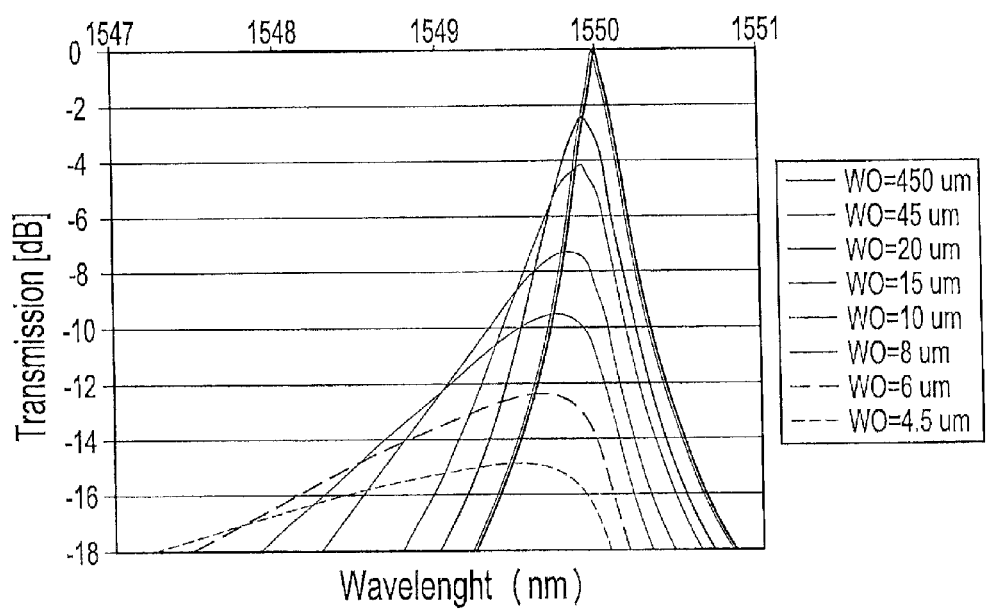
FIG. 16 is graph showing simulation of transmission spectra of a FP cavity for different radii of a Gaussian incident light beam.

Furthermore, a fiber of gradient-index (GRIN) 112 can be merged with the single mode input fiber 108 at the end of this fiber 108 in order to increase the diameter of the incident light beam. It has been demonstrated that the diameter of the light beam can constitute a source of problems by causing losses in the tunable dispersion compensator 100. For example, in the case of the FP filter 40 of FIG. 4, losses due to a small diameter of the light beam can theoretically reach 10 dB and more, as can be seen in FIG. 16. A small diameter of the light beam can explain the experimental transmission losses obtained by typical filters.

Figure 17:
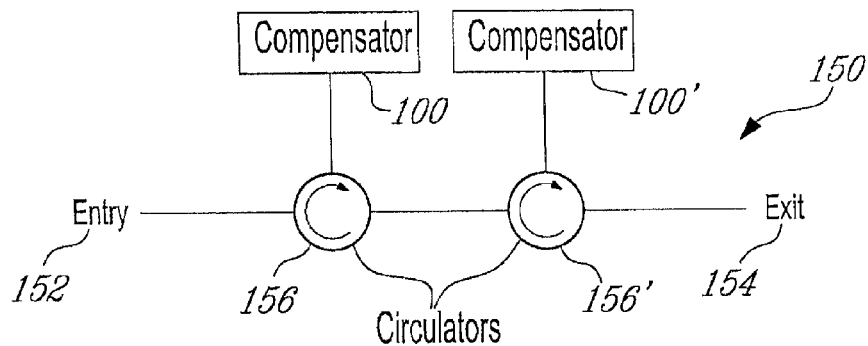
FIG. 17 is a schematic diagram of an assembly comprising two tunable dispersion compensators according to FIG. 15 connected in series.

In order to compensate for the dispersion induced by an optical fiber, the group delay shall vary linearly as a function of the wavelength for each transmission channel. This condition is met by positioning in series two tunable dispersion compensators such as 100 in FIG. 15. The new assembly 150 is shown in FIG. 17. The assembly 150 comprises an input 152 and output 154. Furthermore, each of the two tunable dispersion compensators 100 and 100' is connected to a circulator 156 and 156' respectively, for directing the light according to the direction of each circulator. For example, the light entering through the input 152 will propagate through the circulator 156, then to the compensator 100, then to the circulator 156, then to the circulator 156', then to the compensator 100', then to the circulator 156' and finally will exit through the output 154. The two circulators 156 and 156' are connected in series between the input 152 and the output 154 (FIG. 17).

The GT cavity 102 of the compensator 100 may have a length d=435 μm, for example. The number of silicon layers of the mirror 104 can be selected so as to adapt to particular requirements of a telecommunication network, which may comprise, for example, a spacing of 0.8 nm between each channel and a channel width of 0.24 nm. The slope thus obtained (85 ps/nm) is positive for a displacement of 60 nm of the GT cavity 102 of the first compensator 100 and of 0 nm for the GT cavity 102 of the second compensator 100' placed in series with the first compensator 100. The displacements can be performed using combs such as 53 and 54 of FIG. 4.

However, it is also possible to obtain a negative slope of same amplitude as the positive slope, by varying the displacements of the GT cavities 102. Also, reflectivity of the Bragg reflector 104 can be also changed by adding additional layers. And finally more than two (2) tunable dispersion compensators, such as 100 can be used in order to obtain steep slopes over large channels.

Figure 18:
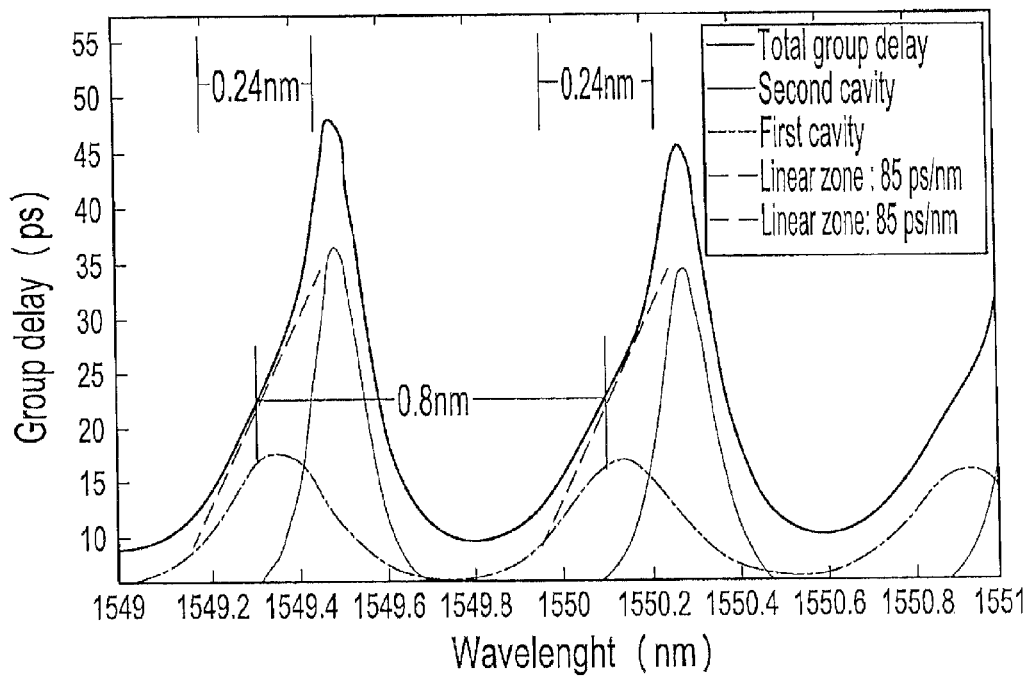
FIG. 18 is a graph showing simulation of a group delay as a function of the wavelength in the assembly of FIG. 17.

FIG. 18 shows a simulation of the delay group as a function of the wavelength in the assembly 150, using two identical tunable dispersion compensators 100 placed in series. The simulation is performed using the method of transfer matrix as mentioned hereinabove. This method is capable of determining the complex reflection coefficient (r) of any multi-layer systems. The phase of the complex reflection coefficient is used to calculate the group delay GP as follows:

$$GP = d\phi/d\omega \quad (3)$$

where $\phi=a \tan [Re(r)/Im(r)]$ and $\omega$ is the angular frequency of the light wave.

Figure 19A:
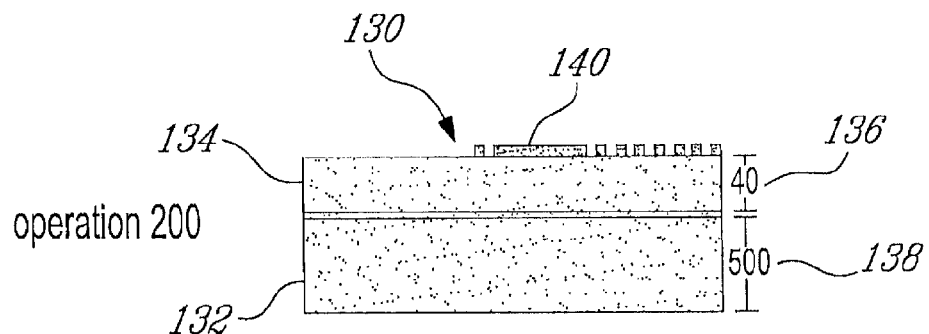
FIGS. 19a)-19g) are schematic views of operations involved in micro-fabricating the tunable dispersion compensator of FIG. 15 comprising a tunable Gires-Tournois cavity (GT cavity)

Referring to FIGS. 19a)-19g), a process 130 for fabricating the tunable dispersion compensator 100 using a GT cavity 102 will be described.

The fabrication process 130 uses, for example, a multi-layer substrate 132, for example a Silicon On Insulator (SOI) wafer comprising a first 40 μm thick Si layer 134 sitting on top of an intermediate 2 μm thick Si oxide layer 136 and a bottom 500 μm thick Si layer 138.

The multi-layer substrate 132 (SOI wafer) also comprises a thick masking layer 140 applied on top of the Si layer 134 for purposes similar to those described hereinabove with reference to FIG. 3 describing a process of fabricating a FP cavity 34. More specifically, the thick masking layer 140 can be similar to the thick masking layer 35 of FIG. 3b).

FIG. 19a)

In operation 200 of fabrication process 130, a conventional photolithography operation is performed on the mask layer 140 to remove portions of the mask layer 140 in order to pattern a mask.

FIG. 19b)

Figure 19B:
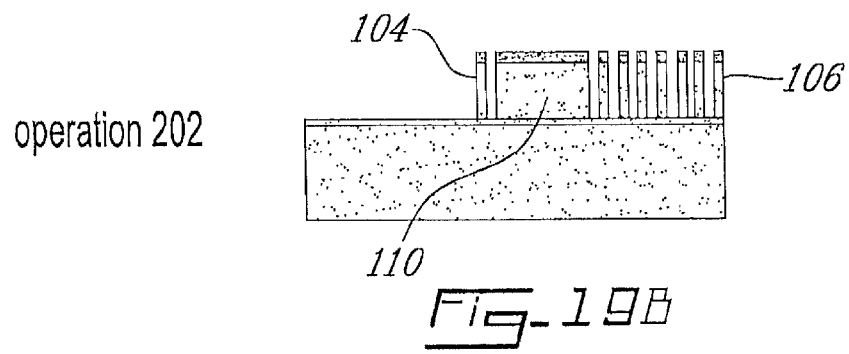
Figure 19C:
Figure 19D:
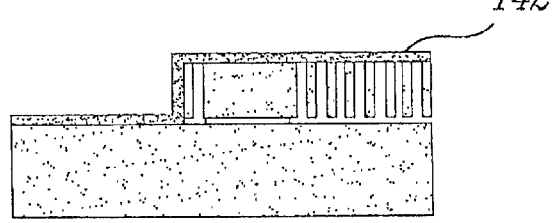
Figure 19E:
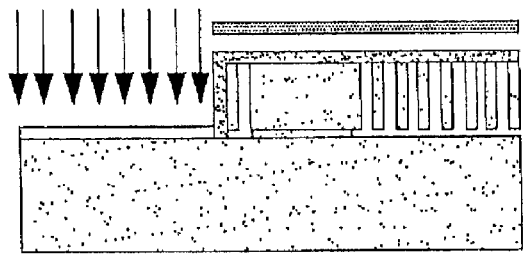
Figure 19F:
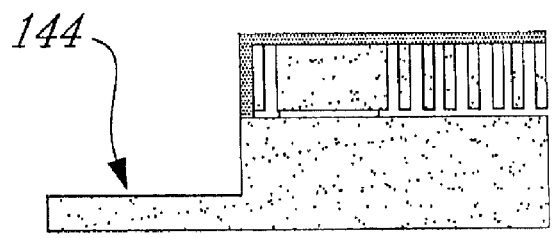
Figure 19G:
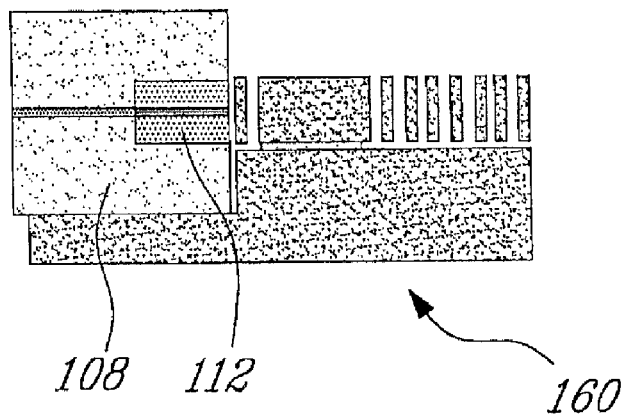

Operation 202 performs a DRIE on the multi-layer substrate 132 (SOI wafer) with a depth of 40 μm for defining the mirrors 104 and 106 (FIG. 15), and the length and width of the waveguide 110. The DRIE operation also defines the length and width of the structures of an electrostatic mechanism such as the comb drive actuator of FIG. 4 and the first 40 μm depth of the groove 144 for optical fiber alignment. As illustrated in FIG. 19b), the DRIE operation is performed through the 40 μm thickness of the Si layer 134.

FIG. 19c)

In operation 204, the intermediate layer 136 and the masking layer 140 are etched away in such a way as to release the mirror 104, which is mobile, and the mobile parts of the electrostatic comb actuator. However, the waveguide 110 is not completely released. Also, the mirror 106 stays fixed on the multi-layer substrate 132 (SOI wafer). For example, liquid Hydrogen Fluoride (HF) can be used to perform this etching. Again, a $CO_2$ drying can then performed in order to prevent the etched structures from sticking.

FIG. 19d)

In operation 206, a layer of resin 142 is applied on top of the etched multi-layer substrate 132 (SOI wafer).

FIG. 19e)

Then, in operation 208, a second photolithography is performed.

FIG. 19f)

In operation 210, the second photolithography consists of a second vertical etching process, using for example DRIE or any other suitable etching process, performed through the bottom 500 μm thick Si layer 138 to define entirely the fiber alignment groove 144.

FIG. 19g)

In operation 212, an optical fiber, such as a single mode fiber 108, is aligned with the mirrors 104 and 106 by placing it into the fiber alignment groove to complete the tunable dispersion compensator 100. As explained herein above, a fiber of gradient-index (GRIN) 112 can be merged with the single mode input fiber 108 at the end of this fiber 108 in order to increase the diameter of the incident light beam.

5.3 High Resolution Integrated Microfluidic Fabry-Perot Refractometer in Silicon Using a Fabry-Perot Cavity A third example of application using a silicon Fabry-Perot cavity according to the present invention consists of a high resolution integrated refractometer for microfluidic systems.

The measurement of the refractive index of fluids, including gases and liquids has been an important field of research, since it is related to many physical parameters of materials. Recently, a lot of work has been done toward the integration of refractive index sensors to microfluidic systems [9]. Many sensors measure the interaction of an evanescent wave at the interface between the sample and a metal (surface plasmon resonance) or a dielectric (integrated waveguide, microactivities). These methods allow very high resolution measurements, sometimes better than $10^{-8}$, but the interaction depth at the interface with the sample is typically smaller than 1 µm, limiting the possibilities to measure the refractive index of bigger biological specimens such as cells. Single cell measurement is of great interest since it is low-cost, label-free, and can be linked to the state or nature of a cell. For example, the effective refractive index can be related to the size of protein level of normal versus cancerous cells [10] or to the structure of a specific cell through the excitation of transverse modes in a Fabry-Perot cavity [11].

Therefore, these applications require a FP cavity with mirror spacing of the order of a cell diameter, as well as integration to microfluidic systems. The above described FP cavity meets with the above-mentioned requirements. The FP cavity offers a simple fabrication process, an easy alignment of optical fibers and high resolution and robustness in measurements.

Figure 20:
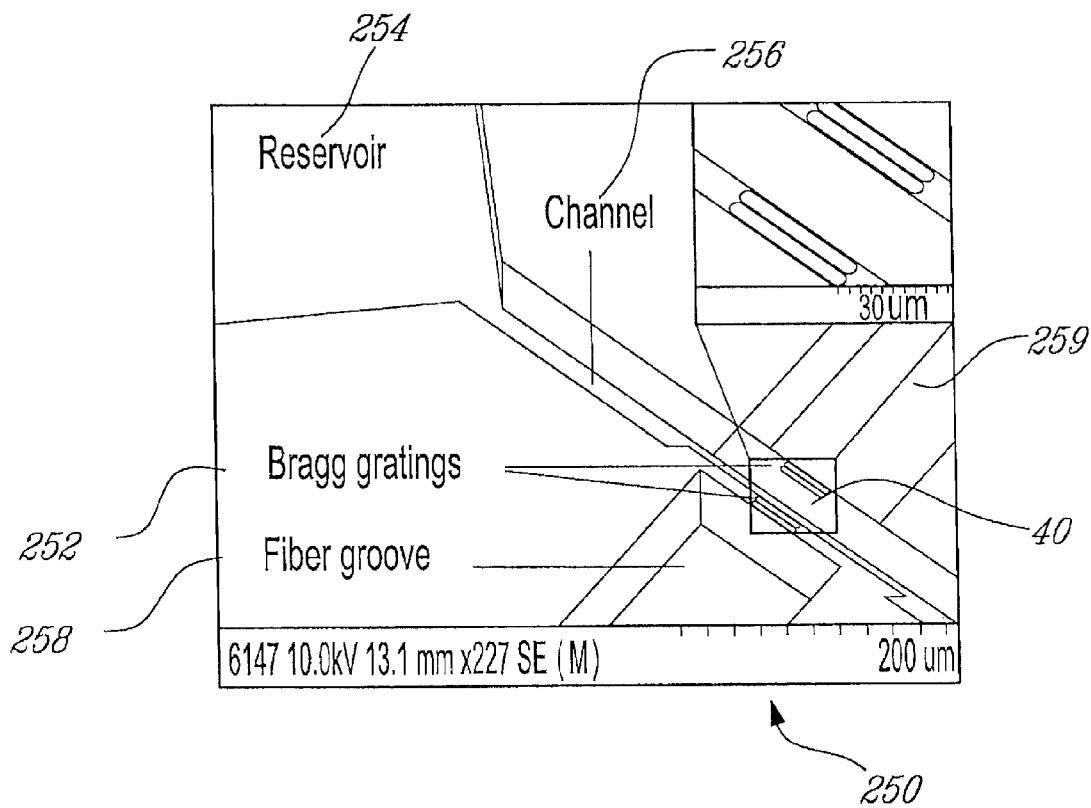
FIG. 20 is a SEM (Scanning Electron Micrograph) photograph of a FP cavity integrated with fiber alignment grooves, a microfluidic channel and a reservoir.

Turning now to FIG. 20, the integrated microfluidic refractometer 250 comprising for example the FP cavity 40 of FIG. 4 will be described.

The integrated refractometer 250 includes two Bragg reflectors (Bragg gratings) 252 vertically etched in silicon to form an in-plane Fabry-Perot filter or cavity, such as the FP cavity 40 of FIG. 4. Each Bragg reflector 252 may be made of three layers of silicon and two layers of air as described herein above.

Furthermore, a reservoir 254 is provided for containing the fluid (liquid or gas) to be measured. The fluid flows through a microfluidic channel 256 by capillary effect and reach the FP cavity 40 formed by the two Bragg reflectors 252 and the air gap therebetween. Incident light from a broadband light source (1520 nm-1620 nm, for example) is supplied to the FP cavity 40 through one of the optical fibers, i.e. the input fiber, placed in one 258 of the fiber alignment grooves. Light propagated through the FP cavity is collected by the second optical fiber (the output fiber, not shown), positioned in the other 259 of the fiber alignment grooves. This output fiber is connected to an optical spectrum analyzer (not shown) to complete the measurement.

Again the fiber alignment grooves 258 and 259 perform easy alignment of the corresponding ends of the input and output optical fibers with the FP cavity 40. This fiber alignment process does not require any preparation step, such as reflective coating or splicing to collimating optics components.

The length of the FP cavity can be designed from one to more than a hundred microns, depending on the targeted application.

In operation, when the fluid is injected in the FP cavity 40 through the microfluidic channel 256, a variation of the refractive index induces a shift of the resonance wavelength. This shift can be detected by the refractometer 250 and analysed by the above mentioned optical spectrum analyzer (not shown) to complete the measurement. For example, a sensitivity of 920 nm/RIU (Refractive Index Units) and a resolution of less than $10^{-3}$ RIU can be obtained in the measurements performed by this integrated microfluidic refractometer 250.

The Bragg reflectors 252, microfluidic structures (reservoir 254 and channel 256) and fiber alignment grooves 258 and 259 can be fabricated simultaneously in one conventional microfabrication process. Indeed, the integrated refractometer 250 can be defined by a single photolithography step. Then, the multi-layer substrate (SOI wafer) is etched by deep reactive ion etching (DRIE). The etch depth can be 70 µm to allow the use of 125 µm diameter conventional SMF 28 optical fibers, for example. The low roughness and high verticality of the optical surfaces are ensured by optimization of a BOSCH process, for example [12].

The photomask used during the photolithography step is designed with 2.6 µm and 1.7 µm thick walls for silicon and air respectively. These thicknesses correspond approximately to the $23^{rd}$ order for the silicon layers and to the $5^{th}$ order for air layers. Of course, those values can be modified according to the fabrication process because of the diffraction effects through the small openings of the photomask and because of a typical 300 nm undercut of silicon during the DRIE process.

The length of the FP cavity 40 is chosen such that the phase shift of the wavelength experienced by the reflection on a Bragg reflector 252 is negligible compared to the phase shift experienced during a round trip of the light in the FP cavity 40, thus improving the sensitivity of the integrated microfluidic refractometer 250. The chosen length of the FP cavity 40 can be 25 µm, for example. It is possible to design a FP cavity 40 of any length between one to more than a hundred microns. A smaller length would decrease the sensitivity and increase the free spectral range of the FP cavity. This could be useful in applications where measurements are to be performed over a large range of refractive indexes. The flexibility of photolithography could also allow a variation of the microchannel width to trap cells in the FP cavity, for example.

Figure 21A:
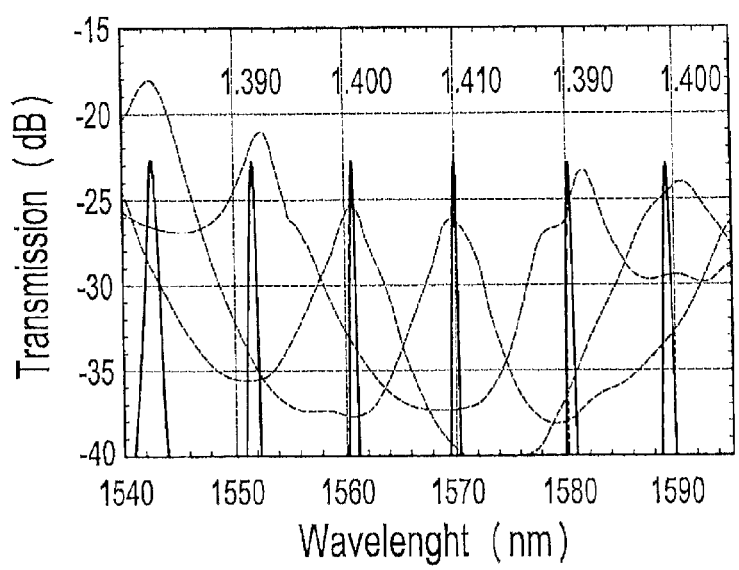
FIGS. 21a)-21b) are graphs showing measured and simulated transmission spectra of the FP cavity of FIG. 20 filled with calibration liquids.

Now turning to FIG. 21, the experimental and simulated results on the transmission of the FP cavity 40 filled with a calibration liquid will be explained.

It should be noted that the measurements are performed with certified refractive index liquids with low temperature dependence (0.0004 RIU/° C.). The simulated results are obtained by the transfer matrix method, considering a plane wave incident on perfectly parallel and flat surfaces [12].

Simulations considering the effects of a Gaussian beam and of verticality deviation of the walls could explain the transmission losses, as well as the broadening of the resonance peaks [13]. These effects are taken into consideration by subtracting 23 dB from the simulated results.

The dimensions of the walls are measured in top plan view with a scanning electron microscope, showing an increase of about 1.1 µm of the thickness of air layers caused by diffraction during the photolithography. For the simulation, the thickness of the silicon walls was reduced by 300 nm at each interface to take into account the undercut of the DRIE process. These values can be adjusted, respectively to 1.086 µm and 314 nm, so as to conform with the experimental results.

Figure 21B:
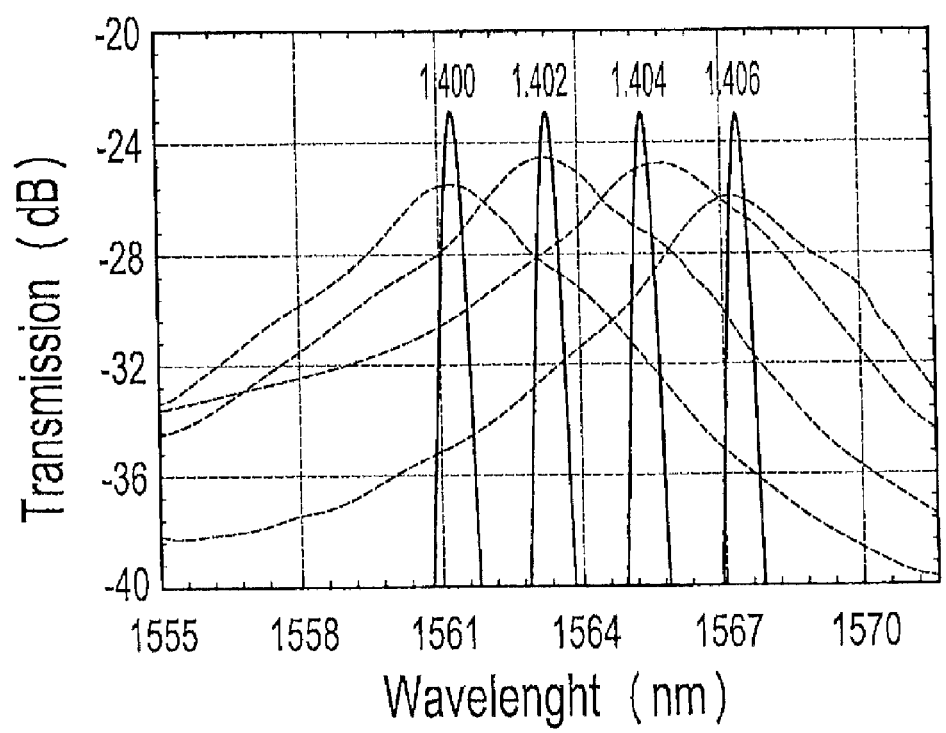

The integrated microfluidic refractometer 250 has a sensitivity of 920 nm/RIU and was able to detect experimentally variations of $\Delta n=2 \cdot 10^{-3}$ of the refractive index, as shown in FIG. 21(b). For this value of $\Delta n$, the peaks were very easily distinguishable. Therefore a resolution of less than $10^{-3}$ can be reached. The integrated microfluidic refractometer 250 is very robust and produces highly reproducible measurements. Indeed, the optical fibers were removed in order to clean the integrated refractometer 250 with acetone and IPA between each measurement. This was done more than 30 times, out of the cleanroom environment, and the integrated refractometer 250 still produced the same spectrum for a given liquid.

5.4 Optical Attenuator Using a Tunable Fabry-Perot Cavity

A fourth example of application using a silicon MEMS Fabry-Perot cavity according to the present invention consists of an optical attenuator.

The function of an optical attenuator is to attenuate the transmission of a FP filter. As will be described in the following description, an example for achieving this function is to displace the inner wall of one of the Bragg reflectors (or mirrors).

Figure 22:
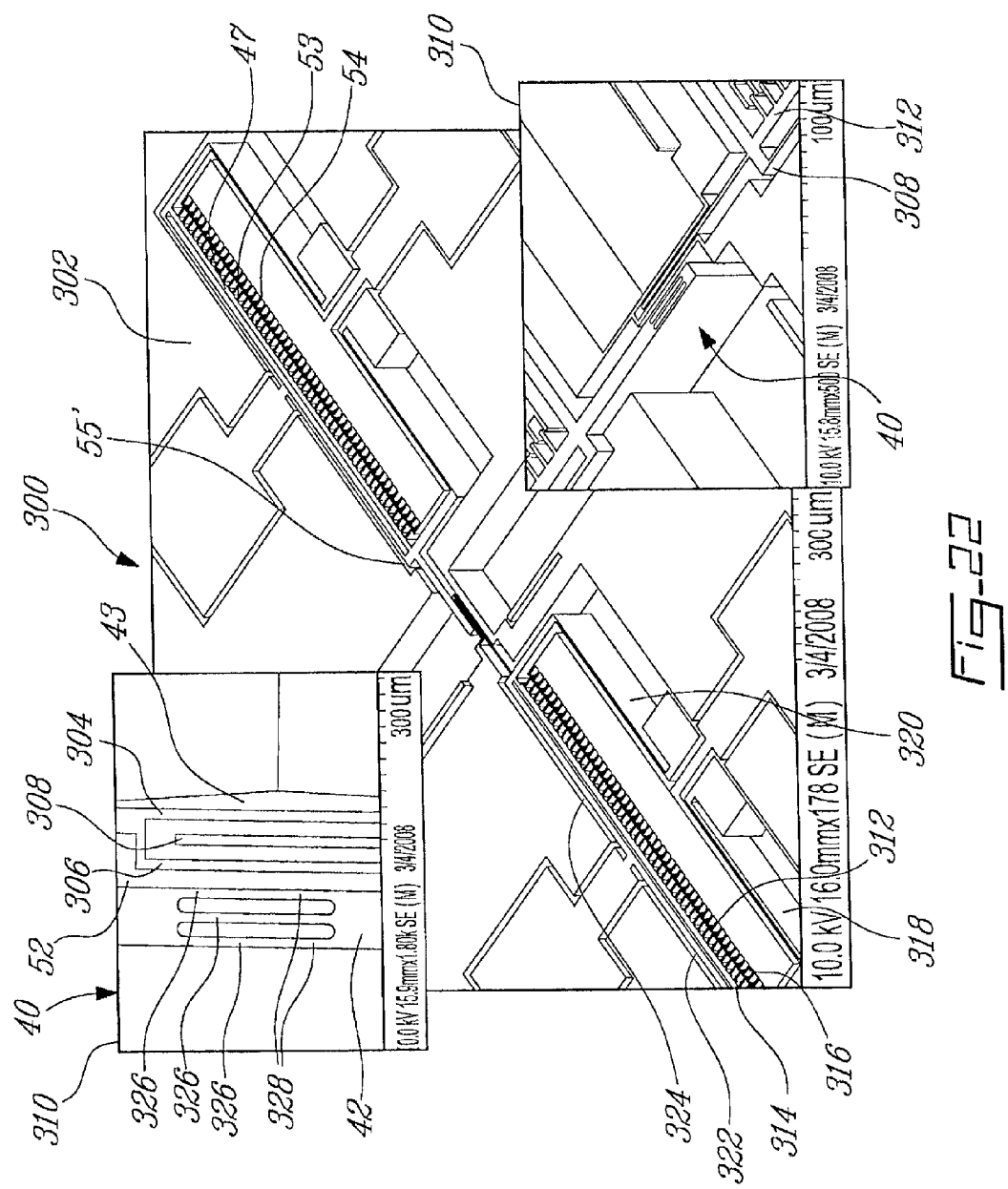
FIG. 22 is a schematic diagram of an optical attenuator comprising a tunable Fabry-Perot according to one embodiment of the present invention.

Turning now to the embodiment of FIG. 22, the optical attenuator 300 comprises a FP cavity, such as the FP cavity 40 of FIG. 4.

FIG. 22 is a Scanning Electron Micrograph (SEM) showing the optical attenuator 300 fabricated using, for example, the fabrication process of FIG. 3.

As illustrated in FIG. 22, the optical attenuator 300 includes a FP cavity 40 comprising two (2) Bragg reflectors 42 and 43 separated by an air gap 52 (see inset 310 of FIG. 22).

The Bragg reflector 42 is made of three (3) silicon walls 326 and two (2) air gaps 328. The Bragg reflector 42 is mobile about a multi-layer substrate 302. The multi-layer substrate 302 can be similar to the multi-layer substrate 30 of FIGS. 3a)-3d). The mobile reflector 42 is connected to the comb drive 47 through the arm 55' (see FIG. 4).

The Bragg reflector 43 comprises an inner silicon wall 306, a central silicon wall 308 and an outer silicon wall 304. A first air gap is present between silicon walls 306 and 308, and a second air gap is present between walls 304 and 308. The silicon walls 304 and 306 of the Bragg reflector 43 are stationary or fixed about the multi-layer substrate 302.

The central wall 308 of the Bragg reflector 43, interposed between the two fixed walls 304 and 306, is mobile. More specifically, the central silicon wall 308 can be displaced through a second electrostatic mechanism similar to the electrostatic mechanism as described with reference to FIG. 4 for displacing the mobile Bragg reflector 42. This second electrostatic mechanism comprises a comb drive actuator provided with a comb drive 312 connected to the central silicon wall 308. The comb drive 312 is similar to the comb drive 47 (see FIG. 4) for moving the mobile central wall 308 and thereby change the reflectivity characteristics of the FP cavity 40.

The comb drive actuator of the second electrostatic mechanism comprises a stationary or fixed comb 316 and the comb drive 312 comprises a comb 314 imbricated with a fixed comb 316. The comb drive 312 is connected to the fixed Bragg reflector 43 through the inner wall 308. The comb drive 312 is suspended from the multi-layer substrate 302 by and is therefore movable with respect to the substrate 302 through a set of four springs 318, 320, 322, and 324. Of course, movement of the comb drive 312 is transmitted to the central silicon wall 308. A number of springs different from four (4) can obviously be used.

Applying a voltage difference between the two combs 314 and 316 will make the combs 314 and 316 to move closer to each other so as to move the central wall 308 within the space between the fixed walls 304 and 306.

As already described with reference to FIG. 4, a Fabry-Perot cavity such as 40 can be tuned by varying the thickness of the air gap 52 between the two reflectors 42 and 43 through an electrostatic mechanism.

The embodiment of FIG. 22 provides an additional way of tuning the Fabry-Perot cavity 40 by moving the central wall 308 within the space between the fixed walls 304 and 306 as described hereinabove in connection with FIG. 22. By so moving the central wall 308, the spectrum of the reflectivity and transmission of the FP cavity 40 is changed.

Figure 23:
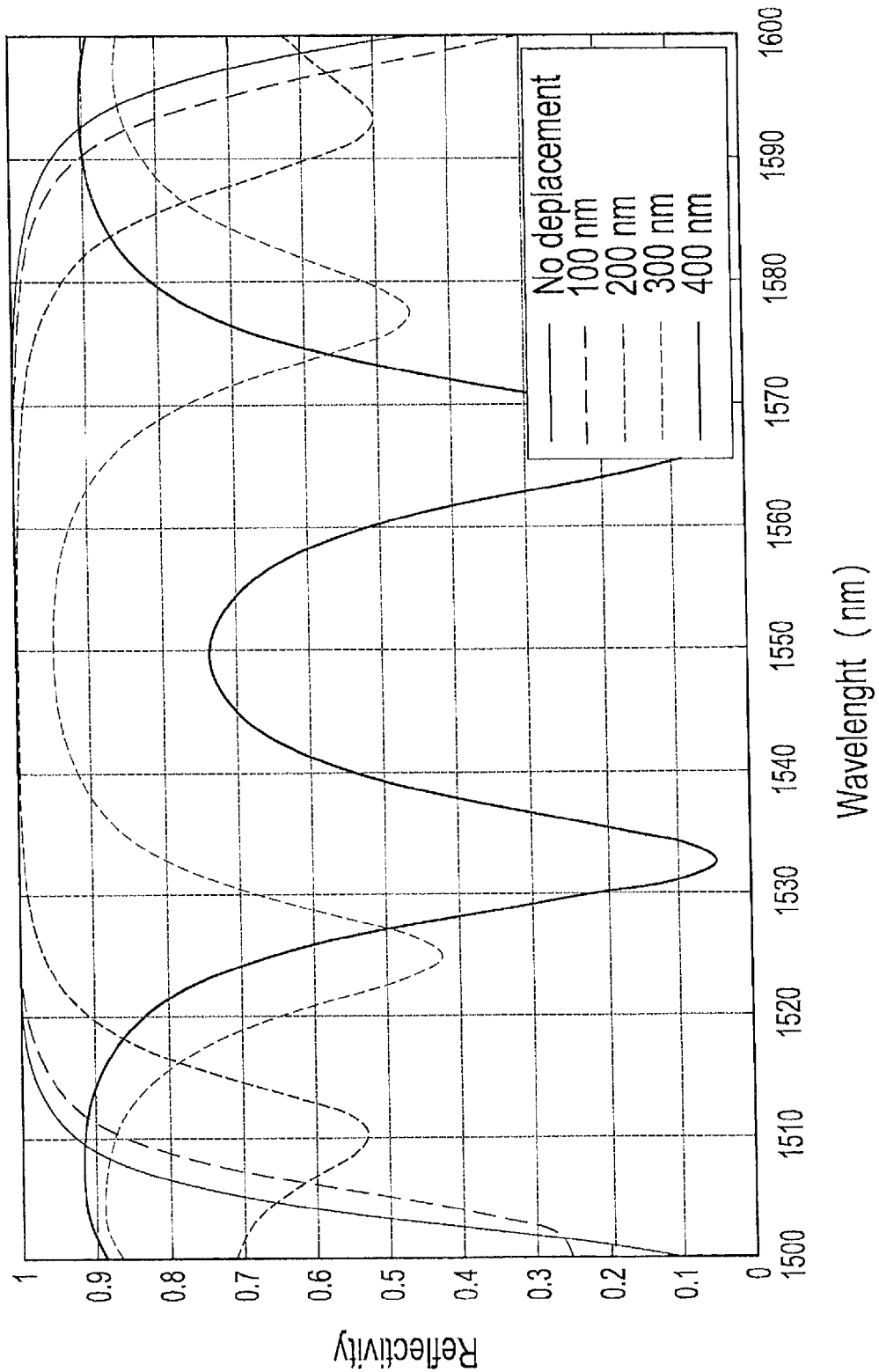
FIG. 23 is a graph showing the reflection spectrum for a Bragg reflector comprising three (3) silicon layers of order 21 and two (2) air layers of order 11 with the inner wall displaced within a range of 0-400 nm.

FIG. 23 shows an example of the effect on the reflectivity spectrum of moving the central wall 308 from 0 to 400 nm between the silicon walls 304 and 306. The silicon layer thicknesses are 2.4 µm and of order 21, the air layer thicknesses are 2 µm and of order 5 for each Bragg reflector 42 and 43, for example. The FP cavity 40 has an air gap of initial thickness of 2.8 µm.

By moving the central wall 308 towards the fixed wall 304 by 400 nm, for example, the thickness of the air gap between the central wall 308 and the fixed wall 306 increases by 400 nm, whereas the air gap thickness between the central wall 308 and the fixed wall 304 decreases by 400 nm. In FIG. 23, it can be seen that the central wavelength of reflection does not change, but it is attenuated, since periodicity of the FP cavity has been broken. Also, the transmission of the FP cavity becomes almost zero for given wavelengths.

Figure 24:
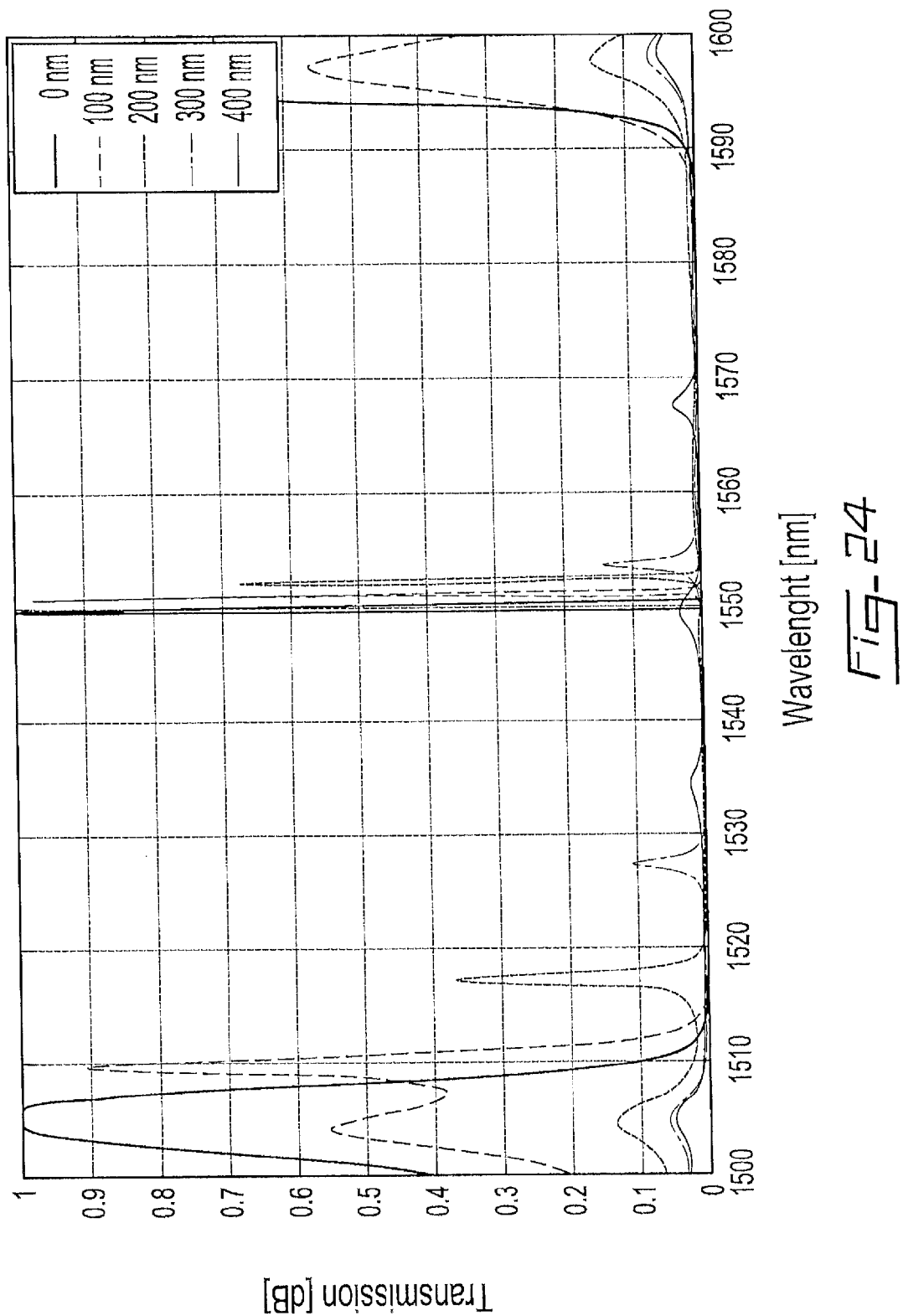
FIG. 24 is a graph showing the transmission spectrum of a Fabry-Perot cavity in which the inner wall of one of the Bragg reflectors, comprising three (3) silicon layers and two (2) air layers, is displaced within a range of 0-400 nm.

FIG. 23 shows that the spectrum of the reflectivity of the FP cavity 40 substantially changes when the central wall 308 of the reflector 43 is moved by more than 200 nm. By sufficiently moving the inner wall 308, periodicity of the FP cavity can be broken and reflectivity at the central wavelength of reflection can be lost. It is possible to use this property to adjust the characteristics of the optical attenuator 300. Indeed, the central wall 308 can be moved until reflectivity of the FP cavity has decreased to the desired level. As shown in FIG. 24, this will also affect to a corresponding level the transmission of the central wavelength.

Figure 25:
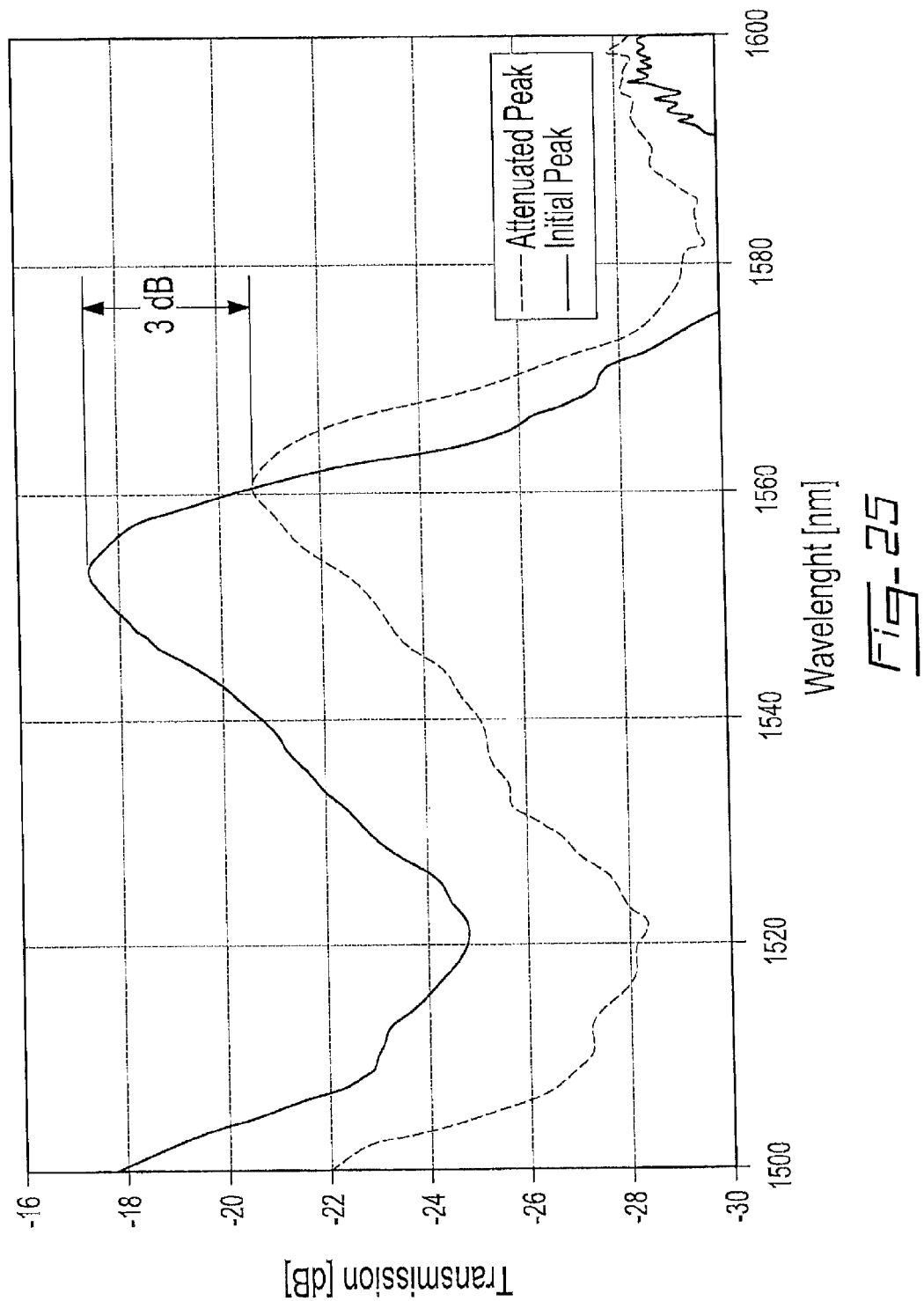
FIG. 25 is a graph illustrating a 3 dB transmission attenuation performed by the optical attenuator of FIG. 22.

FIG. 25 shows a 3 dB attenuation of a transmission peak of a FP cavity through displacement of the central wall 308.

It should be noted that the thickness of the air gaps between the mobile central wall 308 and the fixed walls 304 and 306 is small, about 2 µm. Fabrication of such a thin air gap is complex since the etching process at such restricted area is delicate. Also, a longer etching process is required in order to release the central wall 308 from the multi-layer substrate 302, which leads to overetching and a change in the verticality of the silicon layers of the Bragg reflector 43. Also, it is difficult to obtain an aperture at the bottom of the central wall 308 that is as large as that on top of the central wall 308. For these reasons, the performance of a FP cavity having small air gaps between the walls 304-308 can be reduced.

It should be mentioned that longer FP cavities will have transmission peaks less sensitive to the displacement of the central wall 308 of the fixed Bragg reflector 43. When the FP cavity is designed for varying its length, the transmission peaks can be displaced within a stopband, which is given by the reflectivity spectrum of the Bragg reflector. The length of the FP cavity can be varied, for example, by longitudinally moving one of the two Bragg reflectors. For example, a longitudinal displacement of 500 nm is needed in order to obtain a non-sensitive FP filter.

In a possible design in which the silicon walls 304, 306 and 308 of the Bragg reflector 43 can be moved like an accordion, it has been shown that the central wavelength of reflection is shifted to a shorter wavelength. For example, by moving the walls 304, 306 and 308, the thickness of the two air gaps (between walls 306 and 308 and between walls 304 and 308) can be decreased by 200 nm. By doing this, the wavelength range of the transmission peak is decreased.

Although the present invention has been described hereinabove by way of illustrative embodiments thereof, these embodiments can be modified at will within the scope of the appended claims without departing from the spirit and nature of the subject invention.

6. References

[1] S.-S. Yun, K.-W. Jo, J.-H. Lee, "Crystalline Si-based in-plane tunable Fabry-Perot filter with wide tunable range,"

in *IEEE/LEOS International Conference on Optical MEMS and Their Applications*, pp 77-78, 2003.

[2] A. Lipson, E. M. Yeatman, "Free-space MEMS tunable optical filter on (110) silicon", in *International Conference on Optical MEMS and Their Applications*, Oulu, Finland, 2005, pp. 73-74, IEEE/LEOS.

[3] B. Saadany, M. Malak, F. Marty, Y. Mita, D. Khalil, and T. Bourouina, "Electrostatically-tuned Optical Filter Based on Silicon Bragg Reflectors", in *IEEE/LEOS International Conference on Optical MEMS and Their Applications*, Big Sky, Mont., 2006, pp. 86-87.

[4] M. W. Pruessner, T. H. Stievater, and W. S. Rabinovich, "Integrated waveguide Fabry-Perot microcavities with silicon/air Bragg mirrors", *Optics Letters*, Vol. 32, No. 5, 2007.

[5] Y.-A. Peter, F. B. Koné, J. Masson and N. Godbout, "Tunable micro-electromechanical grating in silicon," (invited paper) in *SPIE Optomechatronic Micro/Nano Devices and Components II*, Optics East 2006, Boston, Mass., vol. 6376, paper 04, SPIE.

[6] M. Tormen, Y.-A. Peter, Ph. Niedermann, A. Hoogerwerf, R. Stanley, "Deformable MEMS grating for wide tunability and high operating speed," *Journal of Optics A*, vol. 8, no. 7, pp. S337-40, 2006.

[7] M. J. F. Digonnet, Rare-Earth-Doped Fiber Lasers and Amplifiers, Marcel Dekker, 2001.

[8] S. Yamashita and M. Nishihara, "Widely Tunable Erbium-Doped Fiber Ring Laser Covering Both C-Band and L-Band," *IEEE J. Select. Topics Quantum Electron.*, vol. 7, no. 1, pp. 41-43, 2001.

[9] H. Hunt and J. Wilkinson, "Optofluidic integration for microanalysis", *Microfluidics and Nanofluidics*, vol. 4, no. 1, pp. 53-79, 2008.

[10] W. Song, X. Zhang, A. Liu, C. Lim, p. Yap, and H. Hosseini, "Refractive index measurement of single living cells using on-chip Fabry-Perot cavity", *Applied Physics Letters*, vol. 89, pp. 203-901, 2006.

[11] H. Shao, W. Wang, S. Lana, and K. Lear, "Optofluidic intracavity spectroscopy of canine lymphoma and lymphocytes," *Photonics Technology Letters, IEEE*, vol. 20, no. 7, pp. 493-495, 2008.

[12] J. Masson, F. Koné, and Y.-A. Peter, "MEMS tunable silicon Fabry-Perot cavity," *Proceedings of SPIE*, vol. 6717, pp. 671-705, 2007.

[13] A. Lipson and E. Yeatman, "Low loss ID photonic band gap filter in (110) silicon," *Opt. Lett*, vol. 31, pp. 395-397, 2006.

What is claimed is:

1. An integrated microfluidic refractometer for measuring a refractive index of a fluid, the refractometer comprising:
   a Fabry-Perot cavity having layers of silicon vertically through a plane of a substrate, the Fabry-Perot cavity comprising two reflectors each comprising three layers of silicon, wherein, in each reflector, a first layer of air is disposed between a first and a second of the layers of silicon and a second layer of air is disposed between the second and a third of the layers of silicon; and
   a microfluidic channel, horizontally formed in the plane of the substrate and connected to the Fabry-Perot cavity, for carrying the fluid to the Fabry-Perot cavity, wherein the microfluidic channel and the Fabry-Perot cavity are coplanar within the substrate;
   wherein the Fabry-Perot cavity detects a shift of wavelength corresponding to a variation of the refractive index when the fluid passes through the Fabry-Perot cavity.

2. An integrated microfluidic refractometer as defined in claim 1, further comprising a reservoir for containing the fluid to be measured.

3. An integrated microfluidic refractometer as defined in claim 1, wherein the microfluidic channel uses a capillary effect to carry the fluid to the tunable Fabry-Perot cavity.

4. An integrated microfluidic refractometer as defined in claim 1, wherein the refractometer is fabricated through a single photolithography and etching process.

5. An integrated microfluidic refractometer as defined in claim 4, wherein the etching process comprises an optimized bosch processs.

* * * * *